US011525140B2

(12) United States Patent
Tijsterman et al.

(10) Patent No.: US 11,525,140 B2
(45) Date of Patent: Dec. 13, 2022

(54) METHODS FOR TRANSFECTING PLANTS AND FOR REDUCING RANDOM INTEGRATION EVENTS

(71) Applicants: Universiteit Leiden, Leiden (NL); Academisch Ziekenhuis Leiden h.o.d.n. LUMC, Leiden (NL)

(72) Inventors: Marcel Tijsterman, Houten (NL); Maartje Van Kregten, Leiden (NL); Paul Hooykaas, Oegstgeest (NL)

(73) Assignees: UNIVERSITEIT LEIDEN, Leiden (NL); ACADEMISCH ZIEKENHUIS LEIDEN H.O.D.N. LUMC, Leiden (NL)

( * ) Notice: Subject to any disclaimer, the term of this patent is extended or adjusted under 35 U.S.C. 154(b) by 94 days.

(21) Appl. No.: 16/087,199

(22) PCT Filed: Mar. 23, 2017

(86) PCT No.: PCT/NL2017/050182
§ 371 (c)(1),
(2) Date: Sep. 21, 2018

(87) PCT Pub. No.: WO2017/164738
PCT Pub. Date: Sep. 28, 2017

(65) Prior Publication Data
US 2019/0390208 A1 Dec. 26, 2019

(30) Foreign Application Priority Data
Mar. 24, 2016 (EP) ..................... 16162322

(51) Int. Cl.
*C12N 15/82* (2006.01)
(52) U.S. Cl.
CPC ..... *C12N 15/8213* (2013.01); *C12N 15/8201* (2013.01); *C12N 15/8218* (2013.01)
(58) Field of Classification Search
None
See application file for complete search history.

(56) References Cited

U.S. PATENT DOCUMENTS

2018/0298392 A1* 10/2018 Cotta-Ramusino .......................... C12N 9/1241

FOREIGN PATENT DOCUMENTS

WO 2017164738 9/2017

OTHER PUBLICATIONS

Inagaki et al. (PLoS Genet 5.8 (2009): e1000613). (Year: 2009).*
Inagaki et al. (The Plant Cell 18.4 (2006): 879-892). (Year: 2006).*
Inagaki, et al. "Arabidopsis TEBICHI, with Helicase and DNA Polymerase Domains, is Required for Regulated Cell Division and Differentiation in Meristems.", The Plant Cell, vol. 18, p. 879-892, Apr. 2006, American Society of Plant Biologies.
Inagaki, et al., "A Link among DNA Replication, Recombination, and Gene Expression Revealed by Genetic and Genomic Analysis of TEBICHI Gene of *Arabidopsis thaliana*.", Public Library of Science (Genetics), Aug. 2009 | vol. 5 | Issue 8 | p. 1-13.
Alonso et al., Genome-wide Insertional Mutagenesis of *Arabidopsis thaliana*, Science, vol. 301, No. 5633, Aug. 1, 2003, pp. 653-657.
Baulcombe, Fast Forward Genetics Based on Virus-Induced Gene Silencing, Genome Studies and Molecular Genetics, vol. 2, No. 2, Apr. 1999, pp. 109-113.
Becker et al., New Plant Binary Vectors with Selectable Markers Located Proximal to the Left T-DNA Border, Plant Molecular Biology, vol. 20, Dec. 1992, pp. 1195-1197.
Beijersbergen et al., Conjugative Transfer by the Virulence System of Agrobacterium Tumefaciens, Science, vol. 256, May 29, 1992, pp. 1324-1327.
Belhaj et al., Plant Genome Editing Made Easy: Targeted Mutagenesis in Model and Crop Plants Using the CRISPR/Cas System, Plant Methods, vol. 9, No. 1, Oct. 11, 2013, pp. 1-10.
Ceccaldi et al., Homologous Recombination-Deficient Tumors are Hyper-dependent on POLQ-Mediated Repair, Nature, vol. 518, No. 7538, Feb. 12, 2015, pp. 258-262.
Chan et al., Dual Roles for DNA Polymerase Theta in Alternative End-Joining Repair of Double-Strand Breaks in *Drosophila*, Public Library of Science Generics, vol. 6, No. 7, e1001005, Jul. 1, 2010, 16 pages.
Chen et al., Controlled Expression of the Transcriptional Activator Gene virG in Agrobacterium tumefaciens by Using the *Escherichia coli* lac Promoter, Journal of Bacteriology, vol. 173, No. 3, Feb. 1991, pp. 1139-1144.
Chilton et al., Targeted Integration of T-DNA Into the Tobacco Genome at Double-Stranded Breaks: New Insights on the Mechanism of T-DNA Integration, Plant Physiology, American Society of Plant Biologists, vol. 133, No. 3, Nov. 2003, pp. 956-965.
Clough et al., Floral Dip: A Simplified Method for Agrobacterium-Mediated Transformation of *Arabidopsis thaliana*, The Plant Journal, Technical Advance, vol. 16, No. 6, Oct. 1998, pp. 735-743.
De Block et al., Engineering Herbicide Resistance in Plants by Expression of a Detoxifying Enzyme, The European Molecular Biology Organization Journal, vol. 6, No. 9, Sep. 1987, pp. 2513-2518.
De Buck et al., The T-DNA Integration Pattern in *Arabidopsis* Transformants is Highly Determined by the Transformed Target Cell, The Plant Journal, Society for Experimental Biology, vol. 60, No. 1, Oct. 2009, pp. 134-145.

(Continued)

*Primary Examiner* — Charles Logsdon
(74) *Attorney, Agent, or Firm* — Kilpatrick Townsend & Stockton LLP

(57) ABSTRACT

The present disclosure provides methods for transfecting plants and for expressing RNA or polypeptide molecules in plants. In particular, plants having reduced POLQ expression and/or activity are transfected in order to reduce random integration events. The disclosure further provides transfected plants and plant progeny produced by the methods disclosed herein.

14 Claims, 5 Drawing Sheets

Specification includes a Sequence Listing.

(56) References Cited

OTHER PUBLICATIONS

De Pater et al., ZFN-Induced Mutagenesis and Gene-Targeting in *Arabidopsis* Through Agrobacterium-Mediated Floral Dip Transformation, Plant Biotechnology Journal, vol. 7, No. 8, Oct. 2009, pp. 821-835.

De Pater et al., ZFN-Mediated Gene Targeting of the *Arabidopsis* Protoporphyrinogen Oxidase Gene Through Agrobacterium-Mediated Floral Dip Transformation, Plant Biotechnology Journal, vol. 11, No. 4, May 2013, pp. 510-515.

Desfeux et al., Female Reproductive Tissues are the Primary Target of Agrobacterium-Mediated Transformation by the *Arabidopsis* Floral-Dip Method, Plant Physiology, vol. 123, No. 3, Jul. 2000, pp. 895-904.

European Application No. 16162322.8, European Search Report dated Aug. 16, 2016, 4 pages.

European Application No. 17718137.7, Office Action dated Oct. 29, 2019, 4 pages.

Eurasian Application No. 201891919 26, Office Action dated Feb. 25, 2019, 1 page.

Fauser et al., Both CRISPR/Cas-based Nucleases and Nickases can be Used Efficiently for Genome Engineering in *Arabidopsis thaliana*, The Plant Journal, vol. 79, No. 2, Jul. 2014, pp. 348-359.

Fernandez-Vidal et al., A role for DNA Polymerase θ in the Timing of DNA Replication, Nature Communications, vol. 5, No. 4285, Jul. 3, 2014, 10 pages.

Fraley et al., The SEV System: A New Disarmed TI Plasmid Vector System for Plant Transformation, Research Papers, Biotechnology, vol. 3, Jul. 1985, pp. 629-635.

Friesner et al., Ku80- and DNA Ligase IV-Deficient Plants are Sensitive to Ionizing Radiation and Defective in T-DNA Integration, The Plant Journal, vol. 34, No. 4, May 1, 2003, pp. 427-440.

Gallego et al., Ku80 Plays a Role in Non-Homologous Recombination but is Not Required for T-DNA Integration in *Arabidopsis*, The Plant Journal, vol. 35, No. 5, Sep. 1, 2003, pp. 557-565.

Gelvin, Plant Proteins Involved in Agrobacterium-Mediated Genetic Transformation, Annual Reviews Phytopathology, vol. 48, 2010, pp. 45-68.

Hanin et al., Gene Targeting in *Arabidopsis*, The Plant Journal, vol. 28, No. 6, 2001, pp. 671-677.

Hogg et al., Promiscuous DNA Synthesis by human DNA Polymerase θ, Nucleic Acids Research, vol. 40, No. 6, Mar. 2012, pp. 2611-2622.

Huang et al., The *Arabidopsis* ACT11 Actin Gene is Strongly Expressed in Tissues of the Emerging Inflorescence, Pollen, and Developing Ovules, Plant Molecular Biology, vol. 33, No. 1, Jan. 1997, pp. 125-139.

Kent et al., Mechanism of Microhomology-Mediated End-Joining Promoted by Human DNA Polymerase Theta, Nature Structural & Molecular Biology, vol. 22, No. 3, Mar. 2015, pp. 230-237.

Khatodia et al., The CRISPR/Cas Genome-Editing Tool: Application in Improvement of Crops, Frontiers in Plant Science, vol. 7, No. 506, Apr. 19, 2016, 13 pages.

Kleinboelting et al., The Structural Features of Thousands of T-DNA Insertion Sites are Consistent with a Double-Strand Break Repair Based Insertion Mechanism, Molecular Plant, Research Article, vol. 8, No. 11, Nov. 2, 2015, pp. 1651-1664.

Kohler et al., Enhancement of Transformation Rates in Higher Plants by Low-Dose Irradiation: are DNA Repair Systems Involved in the Incorporation of Exogenous DNA Into the Plant Genome?, Plant Molecular Biology, vol. 12, No. 2, Feb. 1989, pp. 189-199.

Koole et al., A Polymerase Theta-Dependent Repair Pathway Suppresses Extensive Genomic Instability at Endogenous G4 DNA Sites, Nature Communications, vol. 5, No. 3216, Feb. 5, 2014, 10 pages.

Lazo et al., A DNA Transformation-Competent *Arabidopsis* Genomic Library in Agrobacterium, Biotechnology, vol. 9, Oct. 1991, pp. 963-967.

Li et al., Involvement of KU80 in T-DNA Integration in Plant Cells, Proceedings of the National Academy of Sciences, vol. 102, No. 52, Dec. 27, 2005, pp. 19231-19236.

Li et al., Multiplex and Homologous Recombination-mediated Plant Genome Editing via Guide RNA/Cas9, Nature Biotechnology, vol. 31, No. 8, Aug. 2013, pp. 688-691.

Liu et al., Efficient Isolation and Mapping of *Arabidopsis thaliana* T-DNA Insert Junctions by Thermal Asymmetric Interlaced PCR, The Plant Journal, vol. 8, No. 3, Sep. 1, 1995, pp. 457-463.

Lowder et al., A CRISPR/Cas9 Toolbox for Multiplexed Plant Genome Editing and Transcriptional Regulation, Breakthrough Technologies, Plant Physiology, vol. 169, No. 2, Oct. 2015, pp. 971-985.

Ma et al., Genome Modification by CRISPR/Cas9, The FEBS Journal, State-of-the-Art review, vol. 281, No. 23, Dec. 2014, pp. 5186-5193.

Mateos-Gomez et al., Mammalian Polymerase Theta Promotes Alternative-NHEJ and Suppresses Recombination, Nature, vol. 518, No. 7538, Feb. 12, 2015, pp. 254-257.

Mestiri et al., Multiple Host-Cell Recombination Pathways Act in Agrobacterium Mediated Transformation of Plant Cells, The Plant Journal, Society for Experimental Biology, vol. 77, No. 4, Feb. 2014, pp. 511-520.

Oosumi et al., Implementing Reverse Genetics in Rosaceae: Analysis of T-DNA Flanking Sequences of Insertional Mutant Lines in the Diploid Strawberry, Fragaria Vesca, Physiologia Plantarum, vol. 140, No. 1, Sep. 1, 2010, pp. 1-9.

Park et al., Agrobacterium T-DNA Integration into the Plant Genome Can Occur Without the Activity of Key Non-Homologous Endjoining Proteins, The Plant Journal, Society for Experimental Biology, vol. 81, No. 6, Mar. 2015, pp. 934-946.

Paszkowski et al., Direct Gene Transfer to Plants, The European Molecular Biology Organization Journal, vol. 3, No. 12, Dec. 1, 1984, pp. 2717-2722.

International Application No. PCT/NL2017/050182, International Preliminary Report on Patentability dated Sep. 25, 2018, 8 pages.

International Application No. PCT/NL2017/050182, International Search Report and Written Opinion dated Jul. 7, 2017, 10 pages.

Roerink et al., Polymerase Theta-Mediated End Joining of Replication-Associated DNA Breaks in C elegans, Genome Research, Cold Spring Harbor Laboratory Press, vol. 24, No. 6, Jun. 2014, pp. 954-962.

Salomon et al., Capture of Genomic and T-DNA Sequences During Double-strand Break Repair in Somatic Plant Cells, The European Molecular Biology Organization Journal, vol. 17, No. 20, Oct. 1998, pp. 6086-6095.

Singer et al., Formation of Complex Extrachromosomal T-DNA Structures in Agrobacterium Tumefaciens-Infected Plants, American Society of Plant Biologists, Plant Physiology, vol. 160, Sep. 2012, pp. 511-522.

Thomas et al., Molecular Analysis of Agrobacterium T-DNA Integration in Tomato Reveals a Role for Left Border Sequence Homology in Most Integration Events, Molecular Genetics Genomics, vol. 278, No. 4, Oct. 2007, pp. 411-420.

Tinland, The Integration of T-DNA Into Plant Genomes, Trends in Plant Science, Reviews, vol. 1, No. 6, Jun. 1996, pp. 178-184.

Tzfira et al., Site-Specific Integration of Agrobacterium Tumefaciens T-DNA via Double-Stranded Intermediates, American Society of Plant Biologists, Plant Physiology, vol. 133, No. 3, Nov. 2003, pp. 1011-1023.

Van Attikum et al., The *Arabidopsis* AtLIG4 Gene is Required for the Repair of DNA Damage, but Not for the Integration of Agrobacterium T-DNA, Nucleic Acids Research, vol. 31, No. 14, Jul. 15, 2003, pp. 4247-4255.

Vergunst et al., VirB/D4-Dependent Protein Translocation From Agrobacterium Into Plant Cells, Science, vol. 290, Nov. 3, 2000, pp. 979-982.

Voytas, Plant Genome Engineering with Sequence-Specific Nucleases, Annual Review of Plant Biology, vol. 64, 2013, pp. 327-350.

Windels et al., T-DNA Integration in *Arabidopsis* Chromosomes. Presence and Origin of Filler DNA Sequences, Plant Physiology, vol. 133, No. 4, Dec. 2003, pp. 2061-2068.

Yousefzadeh et al., DNA Polymerase POLQ and Cellular Defense Against DNA Damage, DNA Repair, vol. 12, No. 1, Jan. 1, 2013, 18 pages.

(56) References Cited

OTHER PUBLICATIONS

Yousefzadeh et al., Mechanism of Suppression of Chromosomal Instability by DNA Polymerase POLQ, Public Library of Science, Genetics, vol. 10, No. 10, e1004654, Oct. 2014, 15 pages.
Zahn et al., Human DNA Polymerase θ Grasps the Primer Terminus to Mediate DNA Repair, Nature Structural & Molecular Biology, vol. 22, No. 4, Apr. 2015, pp. 304-311.
Zhu et al., The Bases of Crown Gall Tumorigenesis, Journal of Bacteriology, vol. 182, No. 14, Jul. 2000, pp. 3885-3895.
Zhu et al., Transgene Structures Suggest That Multiple Mechanisms are Involved in T-DNA Integration in Plants, Plant Science, vol. 171, No. 3, Sep. 2006, pp. 308-322.
Chinese Application No. 201780028985.0, Office Action dated Apr. 20, 2021, 9 pages.
Van Kregten et al., "T-DNA integration in plants results from polymerase-θ-mediated DNA repair", Nature plants 2.11 (2016): 1-6.
Japanese Application No. 2008-549971, Office Action, dated Oct. 11, 2021, 4 pages.
Korean Application No. 10-2018-7030387 , Office Action, dated Sep. 16, 2021, 11 pages.
Ukrainian Application No. A 2018 09638, Office Action dated Nov. 3, 2021, 7 pages.
Argentina Application No. 20170102045, Office Action dated Nov. 15, 2021, 6 pages.
Eurasian Application No. 201891919, Office Action dated Dec. 23, 2020, 4 pages. (2 pages of Original Document and 2 pages of English Translation).
Eurasian Application No. 201891919/28, Office Action dated Apr. 22, 2020, 7 pages. (4 pages of Original Document and 3 pages of English Translation).
European Application No. 17718137.7, Office Action dated Jul. 9, 2020, 4 pages.
Indian Application No. 201847038999, Office Action dated May 13, 2022, 7 pages.
Japanese Application No. 2018-549971, Office Action dated May 30, 2022, 4 pages. (2 pages of Original Document and 2 pages of English Translation).
Japanese Application No. 2018-549971, Office Action dated Mar. 1, 2021, 8 pages. (4 pages of Original Document and 4 pages of English Translation).
Korean Application No. 10-2018-7030387, Office Action dated Mar. 21, 2022, 7 pages. (4 pages of Original Document and 3 pages of English Translation).
Mexican Application No. MX/A/2018/011534, Office Action dated Apr. 25, 2022, 5 pages.
Fromm, et al., Inheritance and Expression of Chimeric Genes in the Progency of Transgenic Maize Plants, Biotechnology, vol. 8, No. 9, Sep. 1990, pp. 833-839.
Chinese Application No. CN201780028985.0, Office Action dated Nov. 26, 2021, 13 pages.
Australian Application No. 2017237643, "First Examination Report", dated Jul. 7, 2022, 5 pages.

\* cited by examiner

METHODS FOR TRANSFECTING PLANTS AND FOR REDUCING RANDOM INTEGRATION EVENTS

FIELD OF THE INVENTION

The present disclosure provides methods for transfecting plants and for expressing RNA or polypeptide molecules in plants. In particular, plants having reduced POLQ expression and/or activity are transfected in order to reduce random integration events. The disclosure further provides transfected plants and plant progeny produced by the methods disclosed herein.

BACKGROUND OF THE INVENTION

Genetic modification of plants by transfection allow alterations in traits such as increased yield, disease and pest resistance, increased vegetative biomass, herbicide tolerance, nutritional quality, drought and stress tolerance, as well horticultural qualities such as pigmentation and growth, and other agronomic characteristics for crop improvement. In addition, genetic modification of plants has been used as a system for the expression of recombinant proteins.

Transfection of plants with nucleic acid is now a common practice that may be carried out by a number of different methods known in the art. However, one disadvantage of the present transfection methods is the production of a relatively large number of random DNA integration events in the host genome. Random integration can have unpredictable and/or deleterious effects on the host organism. Furthermore, integration of DNA into the plant genome is not always desirable, particularly when genetically modified (GMO) plants arouse environmental and political issues. Thus, there remains a need for developing improved systems for expressing transgenes in plants.

SUMMARY OF THE INVENTION

One aspect of the disclosure provides a method for reducing random integration of transfected nucleic acid molecules in a plant cell, said method comprising providing a plant cell with a nucleic acid molecule, wherein POLQ expression and/or activity in said plant cell is reduced.

A further aspect of the disclosure provides a method for transfecting a plant cell with a nucleic acid molecule, the method comprising providing a plant cell with a nucleic acid molecule, wherein POLQ expression and/or activity in said plant cell is reduced.

In preferred embodiments, the methods are used for gene targeting. Specifically, the methods are for producing a plant cell that carries a DNA sequence at a specific site in its genome via genetic recombination.

A further aspect of the disclosure provides a method for expressing an RNA molecule or a polypeptide in a plant cell, the method comprising providing a plant cell with a nucleic acid molecule encoding said RNA molecule or polypeptide, wherein POLQ expression and/or activity in said host cell is reduced.

A further aspect of the disclosure provides a method for producing a plant expressing an RNA molecule or a polypeptide, the method comprising providing a plant cell with a nucleic acid molecule encoding said RNA molecule or polypeptide, wherein POLQ expression and/or activity in said plant cell is reduced, and generating the plant from said plant cell.

Preferably, the nucleic acid molecule is transfected into the plant cell having reduced PolQ expression and/or activity. In some embodiments, the nucleic acid molecule is transiently transfected into the plant cell. Preferably, the nucleic acid comprises a plant expression cassette. Preferably, the plant expression cassette comprises a nucleic acid sequence that encodes a polypeptide or an RNA molecule and regulatory sequences to drive expression. Preferably, the nucleic acid is a nuclease. Preferably, the nucleic acid is a component of a Crispr/Cas system.

In some embodiments, the nucleic acid molecule is integrated at a specific site via genetic recombination into the chromosome of the plant cell (or rather via site-specific genetic recombination or homologous recombination). Preferably, such stable integration results in the expression of a heterologous polypeptide or RNA molecule. In some embodiments, the integration is the result of homologous recombination. In some embodiments such stable integration disrupts or modifies an endogenous gene. In some embodiments, the integration is the result of site-specific recombination.

In some embodiments, said plant cell comprises an antisense oligonucleotide specific for a pre-mRNA encoded by the POLQ gene or a double-stranded RNAi molecule specific for mRNA encoded by the POLQ gene. In some embodiments, the plant cell has a mutated POLQ gene. In some embodiments, the plant cell has a knock-out of the POLQ gene.

A further aspect of the disclosure provides for a plant produced by the methods disclosed herein and the progeny thereof (including seeds). Preferably, said plants and progeny comprise the nucleic acid molecule stably integrated into the genome via genetic recombination (i.e., site-specific integration and not random integration).

In some embodiments of the above, said plant cell is not *Arabidopsis thaliana.*

A further aspect of the disclosure provides for a plant or plant cell wherein POLQ expression and/or activity in said plant or plant cell is reduced and wherein said plant or plant cell is not *Arabidopsis thaliana.* The disclosure further provides the use of said plants and cells for transfecting a nucleic acid molecule.

A further aspect of the disclosure provides for the use of a plant or plant cells having reduced POLQ expression and/or activity for producing a plant expressing an RNA molecule or a polypeptide, wherein a) the nucleic acid molecule encoding said RNA molecule or polypeptide is not integrated into the plant cell chromosome or b) the nucleic acid molecule encoding said RNA molecule or polypeptide is integrated via site-specific genetic recombination or homologous recombination in the chromosome of the plant cell.

DETAILED DESCRIPTION OF THE DISCLOSED EMBODIMENTS

Figure 1:
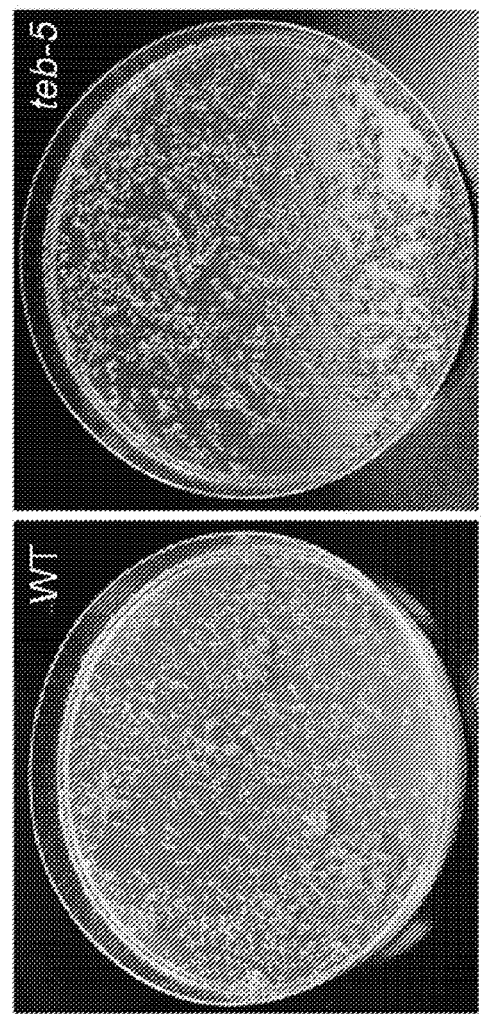
FIG. 1: Pol θ-deficient plants are refractory to T-DNA integration via floral dip transformation. a, Strategy of floral dip transformation: (1) Flowering *A. thaliana* plants are dipped into a suspension containing *Agrobacterium* cells, whereafter (2) the plants are allowed to set seed. (3) The seeds, of which a small percentage may have become transgenic (depicted as yellow), are sown (4) on solidified medium containing the appropriate herbicide as a selection marker. b, Representative images of plates containing the herbicide phosphinothricin (PPT) on which wild-type (left) and teb-5 (right) seeds collected after floral dip transformation are sown. Transformed plantlets, which have stably integrated T-DNA containing the selection marker, are PPT-resistant. c, Floral dip experiments were performed using two different disarmed *Agrobacterium* strains: LBA1100 supplemented with the binary vector pCAMBIA1301, and AGL1, supplemented with the binary vector pSDM3900. d, Representative images of developing embryos transiently expressing an intron-containing GUS reporter gene (gusA) under control of the ACT11 promoter (blue) in the developing silique.
Figure 1:
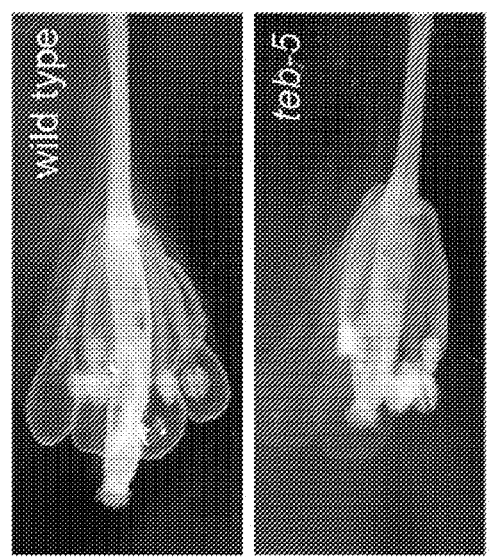
Figure 1:
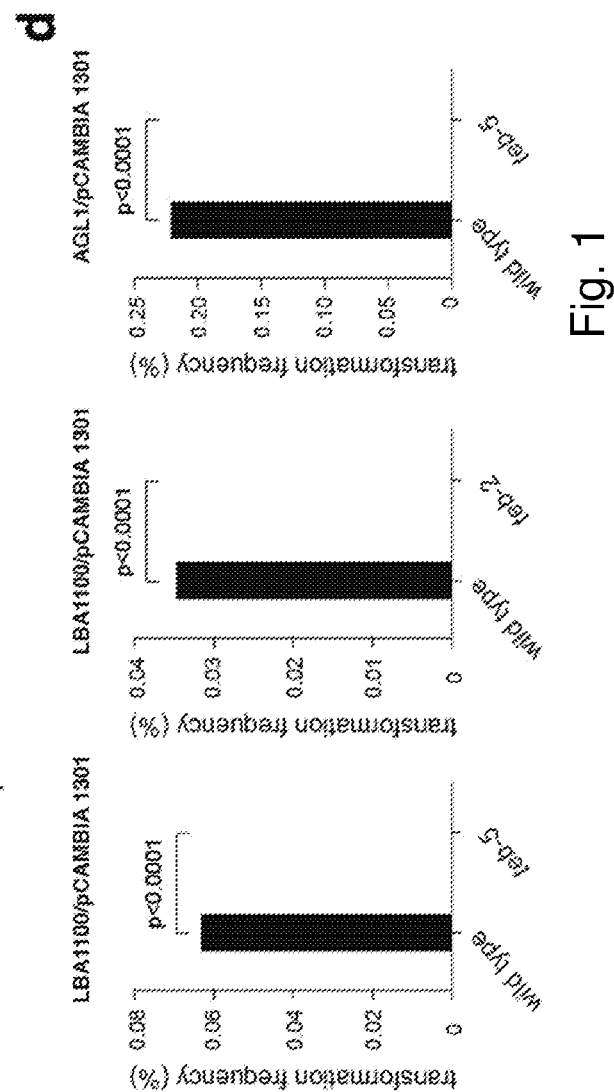

In general, gene recombination in plants is mostly non-homologous, or rather, introduced DNA is randomly inserted into any position of chromosome. Random integration can have deleterious effects if the introduced DNA disrupts, e.g., the expression of an endogenous gene. In addition, the expression of RNA or protein encoded by randomly integrated DNA is less predictable than by site-specific integration since both the site of integration and the number of integration events can effect expression. One of the objects of the methods disclosed herein is to reduce (including to eliminate or avoid) or eliminate random integration of transfected DNA. An additional object of the methods is to provide an efficient method for gene targeting.

In some instances, only transient transfection of DNA is desired in a plant. There may be, e.g., environmental or political reasons to avoid or limit the use of (stably) genetically modified plants. Additionally, in some situations, the desired expression may only be needed for a short time. One of the objects of the methods disclosed herein is to provide methods and plants in which the nucleic acid molecule of interest in only transiently transfected, or rather, the nucleic acid molecule of interest is not inserted into the plant chromosomes. In preferred embodiments, the transfected nucleic acid is a nuclease or a component of the Crispr/Cas system.

One aspect of the disclosure provides methods for transfecting a plant cell with a nucleic acid molecule of interest. The transfected plant cells can be used to express an RNA or a polypeptide of interest. Plants may be generated from such transfected plant cells. Methods are provided for reducing random integration of transfected nucleic acid molecules.

The methods disclosed herein comprise providing a nucleic acid molecule to a plant cell, wherein POLQ expression is the plant cell is reduced. As demonstrated in the examples, transfection of plants having reduced POLQ expression results in the elimination of random integration of the transfected nucleic acid molecule.

In some embodiments, the methods are preferred for transient expression of an RNA or polypeptide of interest. In other embodiments, the methods are preferred for the stable, site-specific integration of the nucleic acid molecule via genetic recombination. Transient expression refers to the expression of a nucleic acid molecule that is not integrated into the host chromosome, but functions independently.

Stable integration refers to the integration of a nucleic acid into the host DNA by covalent bonds. "Genetic recombination" allows introduction in a genome of a selected nucleic acid at a defined site-specific position and includes both homologous recombination and site-specific recombination.

Preferably, the nucleic acid of interest is not inserted via non-homologous recombination. The methods disclosed herein are described as producing cells and plants in which the nucleic acid of interest is not integrated into the plant cell chromosome (i.e., transient transfection) or is integrated via site-specific genetic recombination or homologous recombination in the chromosome of the plant cell. It should be understood to the skilled person that when performing the methods disclosed herein a small percentage of plant cells may be produced in which the nucleic acid of interest has been inserted via non-homologous combination. However, a skilled person can easily identify and disregard such plant cells.

Any suitable nucleic acid molecule may be used for transfecting the plant cell. Although DNA is the preferred nucleic acid molecule, RNA transfection is also encompassed by the invention. For example, An et al. describes an RNA transfection method in *Arabidopsis* (An et al. Biosci Biotechnol Biochem. 2003 December; 67(12):2674-7).

Preferably, the nucleic acid molecule comprises a nucleic acid sequence that encodes a polypeptide or an RNA molecule (e.g., a polypeptide encoding RNA or a non-coding RNA, e.g., long non-coding RNA, microRNA, tRNA, ribosomal RNA, snoRNA, etc.). Nucleic acid molecules of interest include those which impact plant insecticide resistance, disease resistance, herbicide resistance, nutrition and cellulose content, abiotic stress resistance, yield enhancement genes, drought tolerance genes, cold tolerance genes, antibiotic resistance, and marker genes. For example, US20140130207 describes RNAi molecules which can be expressed in plants in order to provide resistance to pests and pathogens.

Preferably, the transfected nucleic acid molecule is heterologous. As used herein, heterologous nucleic acid (or a heterologous gene) includes nucleic acid not normally found in the plant, for example nucleic acid from another species. Heterologous nucleic acid also includes a polynucleotide native to an organism that has been altered in some way (e.g., mutated, added in multiple copies, linked to a non-native promoter or enhancer sequence, etc.). Heterologous plant genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

In some embodiments, the transfected nucleic acid molecule is a nuclease. Preferred nucleases include zinc-finger nucleases (ZFNs), transcription activator-like effector nucleases (TALENs), clustered regularly interspaced short palindromic repeat (CRISPR) nucleases, meganucleases, and nicking endonucleases. Such nucleases may be useful in methods of gene or genome editing.

Preferably, the transfected nucleic acid molecule is part of the Crispr/Cas system, such as a Cas nuclease and/or a guide nucleic acid. As is known to a skilled person, the Crispr/Cas system can be used for gene editing. Genes can be edited, mutated, replaced, or knocked-out using this system. Crispr/Cas can also be used to modulate gene expression by using modified "dead" Cas proteins fused to transcriptional activational domains (see, e.g., Khatodia et al. Frontiers in Plant Science 2016 7: article 506 and Ma et al. FEBS Journal 2014 5186-5193 for recent reviews of Crispr technology).

In preferred methods of the invention, a nucleic acid molecule encoding a Cas protein is transfected. The Cas protein may be a type I, type II, type III, type IV, type V, or type VI Cas protein. The Cas protein may comprise one or more domains. Non-limiting examples of domains include, a guide nucleic acid recognition and/or binding domain, nuclease domains (e.g., DNase or RNase domains, RuvC, HNH), DNA binding domain, RNA binding domain, helicase domains, protein-protein interaction domains, and dimerization domains. The guide nucleic acid recognition and/or binding domain may interact with a guide nucleic acid. In some embodiments, the nuclease domain may comprise one or more mutations resulting in a nickase or a "dead" enzyme (i.e., the nuclease domain lacks catalytic activity).

Preferred Cas proteins include c2c1, C2c2, c2c3, Cas1, Cas1B, Cas2, Cas3, Cas4, Cas5, Cas5e (CasD), Cash, Cas6e, Cas6f, Cas7, Cas8a, Cas8a1, Cas8a2, Cas8b, Cas8c, Cas9 (Csn1 or Csx12), Cas10, Cas10d, Cas10, Cas10d, CasF, CasG, CasH, Cpf1, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In preferred methods of the invention, a Crispr targeting sequence is transfected. Such sequences are known to the skilled person and include gRNA (guide RNA), crRNA, tracrRNA, and sgRNA. The Crispr targeting sequence binds to a complementary sequence in the host plant genome and targets a Cas protein to the respective site.

Transfection of the Crispr/Cas system in a plant cell having reduced POLQ expression and/or activity reduces the random insertion of Crispr/Cas components into the plant genome. While not wishing to be bound by theory, transient transfection of Crispr components may reduce off-targets effects and/or increase specificity of the Crispr/Cas system. In other embodiments, the disclosure provides methods for the generation of plants in which Crispr components (such as a Cas enzyme) are stably transfected via site-specific genetic recombination or homologous recombination.

In some embodiments, the methods provide transient transfection of the nucleic acid molecule. Preferably, the nucleic acid molecule for transient transfection comprises a plant expression cassette. A suitable plant expression cassette comprises 5' and 3' regulatory sequences operatively linked to a nucleic acid sequence encoding a transcript. The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter).

Preferably, a plant expression cassette comprises a promoter that drives expression in plants and a polyadenylation signal. Exemplary promoters for expression of a nucleic acid sequence include plant promoters such as the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue-specific enhancers (Fromm et al., 1986) may also be used. Examples of plant expression vectors include those detailed in: Becker, D. et al., 1992, New plant binary vectors with selectable markers located proximal to the left border, Plant Mol. Biol. 20: 1195-1197; and Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

In some embodiments, the methods provide stable site-specific integration of the nucleic acid molecule via genetic recombination. Site-specific integration refers to integration at a defined region of the genome that is dependent on the nucleic acid sequence in the genome. This differs from random integration. In one embodiment, the nucleic acid integrates into the plant genome via homologous recombination. Suitable methods and vectors for inducing homologous recombination are known. For example, a homologous recombination vector can be prepared comprising the nucleic acid molecule of interest flanked at its 5' and 3' ends by nucleic acid sequences which are homologous to endogenous plant sequences. Homologous recombination can be used, e.g., to replace a wild type gene on a chromosome by an unrelated new gene, an inactivated gene or a modified version of the wild-type gene (new allele). Homologous recombination may also be induced by nucleases such as zinc-finger nucleases (ZFNs), transcription activator-like effector nucleases (TALENs), clustered regularly interspaced short palindromic repeat (CRISPR) nucleases, meganucleases, and nicking endonucleases.

For example, the nucleic acid may encode a mutated form of an endogenous polypeptide or RNA molecule. The mutations may be gain of function or loss of function (e.g., inactivating mutation). In some embodiments, the nucleic acid may comprise, for example, a first region, a second region, and a third region. The first and third regions are substantially homologous to a gene of interest. The second region may comprise a mutated form of an endogenous gene or, e.g., encode a marker. Preferably, the marker is a positive selection marker, such as a drug resistance gene, a gene encoding a surface marker, a gene encoding a fluorescence marker, or a gene encoding β-galactosidase. Suitable homologous recombination methods and vectors for plants are known in the art and are described, e.g., in WO2003027261.

In one embodiment, the nucleic acid integrates into the plant genome via site-specific recombination. Several site-specific recombination systems have been tested in plants including the Cre/lox system, the Flp/FRT system, and the R/RS system. Recombinases exert their effects by promoting recombination between two of their recombining sites. In the case of cre, the recombining site is a Lox site, and in the case of Flp the recombining site is a Frt site. These recombining sites include inverted palindromes separated by an asymmetric sequence. Recombination between target sites arranged in parallel (so-called "direct repeats") on the same linear DNA molecule results in excision of the intervening DNA sequence as a circular molecule. Plants and plant cells carrying stable recognition sequences (e.g., FRT, lox, or RS site) in their genome can be used to transfect a nucleic acid molecule of interest flanked by the respective recognition sequence together with the appropriate recombinase (e.g., Flp, Cre, or R recombinase) in methods disclosed herein. Transfection results in the stable integration of the nucleic acid molecule.

For either transient or stable transfection, selectable or screenable markers can be included in the nucleic acid molecule to be transfected. "Marker genes" are genes that impart a distinct phenotype to cells expressing the marker protein and thus allow transfected cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. (See, DeBlock, et al., (1987) EMBO J. 6:2513-2518; DeBlock, et al., (1989) Plant Physiol. 91:691-704; Fromm, et al., (1990) 8:833-839; Gordon-Kamm, et al., (1990) 2:603-618). For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Many examples of suitable marker proteins are known to the art and can be employed in the practice of the invention. In preferred embodiments of the methods, the transfected plant cells or the regenerated plants thereof are screened for the presence of a selectable or screenable marker.

"Transfection" is defined herein as a process for introducing a nucleic acid into a plant cell and includes the term "transformation". Plant cells and plant parts include single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like. Transfection may occur under natural or artificial conditions using various methods well known in the art. Suitable methods include viral infection, electroporation, lipofection, and particle bombardment. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). Transfection includes the introduction of nucleic acid into a plant cell by physical or chemical methods or through viral infection. However, it is clear to a skilled person that this process does not include the introduction of a nucleic acid by interbreeding or crossing.

The transfected cells may be regenerated to whole plants using standard techniques known in the art. In addition to transfecting in vitro cultivated plant cells, tissues or organs; whole living plants can also be transfected. *Agrobacterium*-mediated transfer is a widely applicable system for introducing genes into plant cells because the DNA can be introduced into whole plant tissues. Suitable processes include dipping of seedlings, leaves, roots, cotyledons, etc. in an *Agrobacterium* suspension which may be enhanced by vacuum-infiltration as well as for some plants the dipping of a flowering plant into an Agrobacteria solution (floral dip), followed by breeding of the transformed gametes.

The successfully transfected cells, which are preferably identified by selection or screening and cultured in an appropriate medium that supports regeneration, will then be allowed to regenerate into plants. "Regeneration" refers to the process of growing a plant from a plant cell (e.g., plant protoplast or explant) and such methods are well-known in the art.

In a preferred embodiment, the nucleic acid molecule of interest is transfected via *Agrobacterium* T-DNA system. Suitable *Agrobacterium* strains include LBA4404, EHA101, C58, EHA105, AGL1, or GV3101. The T-DNA may be a modified Ti plasmid or an artificial vector derived from the Ti plasmid (tumour inducing plasmid), referred collectively herein as a "T-DNA vector". The Ti plasmid is a circular DNA molecule comprising a T-DNA region and a vir (virulence) region. The endogenous T-DNA region comprises the genes for the biosynthesis of auxin (aux), cytokinin (cyt) and opine (ocs) flanked by a right and left border. The borders are imperfect direct repeats having 24 base pairs The genes in the virulence region are responsible for transferring the T-DNA into plant cells. For example, the VirD2 endonuclease with assistance of VirD1 cuts at the borders of the T-DNA, releasing a single stranded copy of the T-DNA, the T-strand, which is transported into plant cells by the virB encoded transport system. The VirE2 protein binds the T-strand in the host cell and the complex enters the plant cell nucleus.

In some embodiments, the nucleic acid of interest is inserted into the T-DNA region of a Ti plasmid. Preferably, the aux, cyt, and ocs genes of the Ti plasmid are removed (i.e., the plasmid is "disarmed").

In some embodiments, an artificial vector derived from the Ti plasmid is used. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety. In some embodiments, one or more genes of the Ti plasmid is mutated to increase transformation efficiency, e.g., such as *Agrobacterium* strains wherein the vir gene expression and/or induction thereof is altered due to the presence of mutant or chimeric virA or virG genes (e.g. Chen and Winans, 1991, J. Bacteriol. 173: 1139-1144; and Scheeren-Groot et al., 1994, J. Bacteriol. 176: 6418-6246). In another embodiment, the *Agrobacterium* strain can comprise an extra virG gene copy, such as the super virG gene derived from pTiBo542.

In a preferred embodiment, a T-DNA binary system is used. In a binary system, the vir genes required for transfer of T-DNA into plant cells and the T-DNA are on separate plasmids. The "binary plasmid" comprises the nucleic acid of interest and, preferably a plant marker, flanked on the left and the right by T-DNA border sequences. The binary plasmid normally also comprises one ore more origin of replication to allow for replication in both *E. coli* and *Agrobacterium* and a bacteria selectable marker. The "helper plasmid" comprises the vir genes from the Ti plasmid. T-DNA binary system vectors are commercially available. A binary vector system wherein the T-region is located on the chromosome of the *Agrobacterium* strain has also been disclosed (see, e.g., EP-B 176 112).

In preferred embodiments of the methods disclosed herein, the methods comprise providing a plant cell with a nucleic acid molecule, said molecule comprising a nucleic acid sequence of interest flanked by a right border sequence (RB) derived from the *Agrobacterium* T-DNA sequence and a left border sequence (LB) derived from the *Agrobacterium* T-DNA sequence. As discussed herein, the nucleic acid molecule may further comprise regulatory sequences to drive expression in plants and/or marker genes. Preferably, a vir domain derived from the Ti plasmid is also provided in the methods. The vir domain may be present on the same nucleic acid molecule described above or may be provided by a separate vector, e.g., a helper plasmid. It is clear to a skilled person that the entire vir domain from the Ti plasmid is not necessary While not wishing to be bound by theory, we believe that the single-stranded unprotected T-DNA 3' end (left border) is normally a substrate for POLQ-mediated repair reaction, which leads to random integration. Reduction of POLQ in the plant cell reduces or eliminates the random integration of T-DNA, while leaving genetic recombination and transient expression unaffected. Accordingly, the reduction of POLQ, is expected to reduce or eliminate random integration when a plant cell is transfected with any source of nucleic acid which results in the presence in the nucleus of a single-stranded DNA with an unprotected 3' end.

In principle all plants can be used for transfection. Preferred transgenic plants are, for example, selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants such as plants advantageously selected from the group of the genus cotton, cantaloupe, radicchio, papaya, plum, peanut, oilseed rape, canola, sunflower, safflower, olive, sesame, hazelnut, almond, avocado, bay, pumpkin/squash, linseed, soya, pistachio, borage, maize, wheat, rye, oats, sorghum and millet, triticale, rice, barley, cassaya, potato, sugarbeet, egg plant, alfalfa, and perennial grasses and forage plants, oil palm, vegetables (brassicas, root vegetables, tuber vegetables, pod vegetables, fruiting vegetables, onion vegetables, leafy vegetables and stem vegetable), buckwheat, Jerusalem artichoke, broad bean, vetches, lentil, dwarf bean, lupin, clover and Lucerne for mentioning only some of them. Preferably, the plant is Corn, Oilseed Rape, Canola, Cotton, Potato, Soybean, Sugar Beet, Squash, Cantaloupe, Rice, Flax, Raddicchio, Papaya, Alfalfa, or Wheat. Most preferred plants are Corn, Cotton, Soybean, Canola and Rice. In a preferred embodiment, the plant cell is not *Arabidopsis thaliana*.

Plants, like all multi-cellular eukaryotes, express polymerase theta, encoded by the POLQ (Pol θ) gene. In the present disclosure, POLQ and polymerase theta are used interchangeably. POLQ comprises a central domain having about 800 residues in plants and a polymerase domain which belongs to the "A" family of DNA polymerases (see, e.g., Yousefzadeh and Wood DNA Repair 2013 12:1-9). The polymerase domain comprises 5 "motifs" (see FIG. 2A of Yousefzadeh and Wood). Sequence homology between plants is is especially conserved in these regions, in particular in motifs 2, 5, and 6.

An exemplary POLQ sequence from plants is the "helicase and polymerase containing protein TEBICHI" from *Arabidopsis thaliana*. The 2154 amino acid protein sequence may be found on the NCBI database under accession number BAD93700.1. The TEBICHI sequence was also published in Inagaki et al. (Plant Cell 18 (4), 879-892 (2006)). The POLQ genes in other plants may be identified, e.g., by performing a BLAST alignment search with the POLQ sequence from *Arabidopsis thaliana*. For example, the POLQ genes from the following exemplary plants are listed in the NCBI database under the following accession numbers:
rice *Oryza sativa*: XP_015619406
potato *Solanum tuberosum*: XP_006356662
soybean *Glycine max*: XP_003545584
sugar beet *Beta vulgaris*: XP_010667709
tomato *Solanum lycopersum*: XP_010325163
banana *Musa acuminata* Sequence ID: ref |XM_009385225.1|
apple *Malus x domestica*: Sequence ID: ref |XM_008380001.1|
grape *Vitis vinifera* Sequence ID: ref |XM_010650232.1|
rapeseed *Brassica napus* Sequence ID: ref |XM_013882859.1|
Orange *Citrus x sinensis* Sequence ID: ref |XM_006476088.2|
corn *Zea mays* Sequence ID: AQK40086

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences.

Alternatively, standard molecular techniques may be used to identify the POLQ gene from a particular plant species. For example, oligonucleotide probes based on the TEBICHI sequence can be used to identify the desired polynucleotide in a cDNA or genomic DNA library from a desired plant species. Probes may be used to hybridize with genomic DNA or cDNA sequences to isolate homologous genes in the plant species of interest.

Alternatively, the POLQ gene can conveniently be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Appropriate primers and probes for identifying the POLQ gene in plant can be generated based on the TEBICHI sequence. For a general overview of PCR see PCR Protocols: A Guide to Methods and Applications (Innis, M, Gelfand, D., Sninsky, J. and White, T., eds.), Academic Press, San Diego (1990).

In the plant cells used in the methods described herein, POLQ expression and/or activity is reduced. The reduction in POLQ expression may occur at the level of nucleic acid or protein. Preferably, the amount of functional POLQ expression is reduced by at least 30%, 40%, 50%, 60%, 70%, 80%, 90%, 95% or 100% as compared to a corresponding wild-type plant cell. Preferably, the expression and/or activity is reduced by at least 50% as compared to a corresponding wild-type plant cell, more preferably, the expression and/or activity is reduced by at least 70%.

In some embodiments, POLQ expression is determined by measuring the expression of POLQ nucleic acid. Suitable methods include RT-PCR, quantitative PCR, Northern blotting, gene sequencing, in particular RNA sequencing, and gene expression profiling techniques, e.g., microarrays. In preferred embodiments, expression is determined by measuring the level of POLQ protein. Suitable methods include ELISAs, immunocytochemistry, flow cytometry, Western blotting, proteomic, and mass spectrometry. Preferably, POLQ expression is determined in an immunoassay. Suitable immunoassays include, e.g., radio-immunoassay, ELISA (enzyme-linked immunosorbant assay), "sandwich" immunoassay, immunoradiometric assay, gel diffusion precipitation reaction, immunodiffusion assay, precipitation reaction, agglutination assay (e.g., gel agglutination assay, hemagglutination assay, etc.), complement fixation assay, immunofluorescence assay, protein A assay, and immunoelectrophoresis assay.

In some embodiments, POLQ activity refers to the ability of POLQ to bind DNA, in particular to chromatin. Such activity can be measured by any method known to a skilled person such as by immunoblotting chromatin fractions with a POLQ antibody as described in Fernandez-Vidal et al., 2014 Nature Communications 5.

In some embodiments, POLQ activity refers to its ability to act as a polymerase. Such activity can be measured, e.g., in the primer extension assay described in Hogg et al. Nucleic Acids Res. 2012 March; 40(6): 2611-2622, an MMEJ assay as described in Kent et al. Nat Struct Mol Biol. 2015 March; 22(3): 230-237. Zhan et al. (Nat Struct Mol Biol. 2015 April; 22(4): 304-311) describes additional assays to measure POLQ activity. As is clear to a skilled person, a reduction in POLQ activity refers to the reduction of activity as compared to the activity of wild-type POLQ from the same organism.

Figure 2:
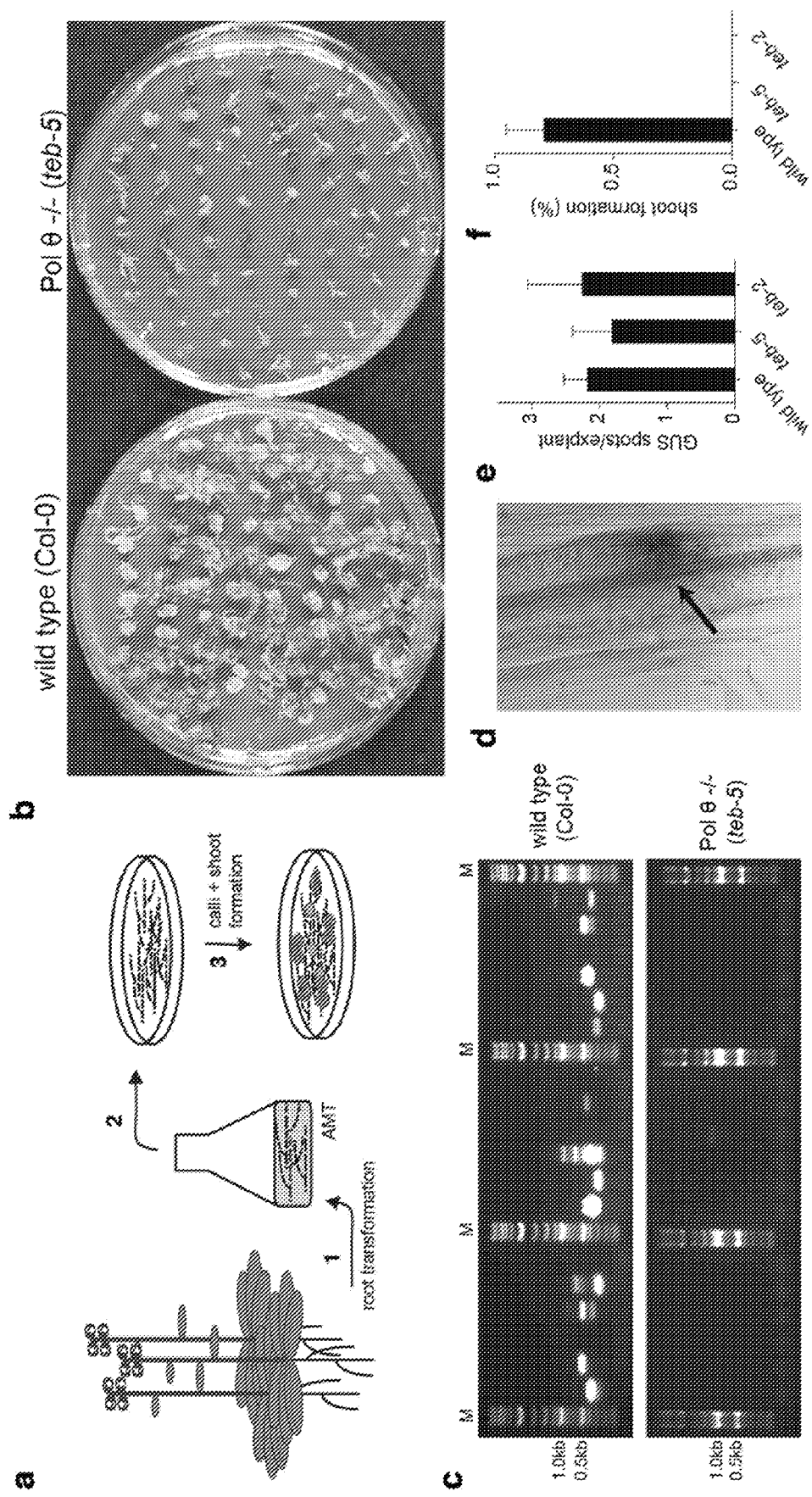
FIG. 2: Pol θ is required for root transformation-mediated *Arabidopsis* transgenesis. a, Strategy of root transformation. Seeds are germinated in liquid culture (1) and roots are collected from 10-days old *A. thaliana* plantlets, precultured for two to three days, on solidified medium and co-cultivated with *Agrobacterium* cells (2). Calli/shoots are allowed to form on solidified medium containing the herbicide PPT and after three weeks transferred to fresh plates, on which shoots that have stably integrated the T-DNA, and have thereby acquired the resistance marker, can continue to grow (3) b, Representative images of plates containing the herbicide phosphinothricin (PPT) on which wild-type (left) and teb-5 (right) roots were grown to allow shoot formation. Wild-type shoots (left panel) have acquired PPT-resistance pointing towards stable T-DNA integration, while teb-5 shoots (right panel) are deteriorating. c, TAIL-PCR to recover T-DNA-plant genome junctions yields products for most wild-type calli (upper panel), while teb-5 calli do not yield any products in TAIL-PCR (lower panel). d, A wild-type root explant in which an arrow points to a GUS-positive spot, where *Agrobacterium* has delivered one or more T-DNAs containing the intron-containing GUS reporter gene. e, GUS-positive spots per explant were counted for wild-type Col-0, teb-2, and teb-5. At least 100 root explants were counted per experiment. f, Formation of green shoots, indicating stable integration of T-DNA, was counted for wild-type Col-0, teb-2 and teb-5.

Down-regulation of POLQ may be accomplished by introducing a mutation that disrupts the gene by decreasing POLQ expression, by abrogating expression entirely, or by rendering the gene product non-functional. For example, the mutation may be a point mutation, an insertion, or a deletion, and the mutation may be located in a coding (e.g., in an POLQ exon) or non-coding portion of the POLQ gene (e.g., in the POLQ promoter region). Yousefzadeh and Wood (DNA Repair, Volume 12, Issue 10, 2013, Page 871) provide structural comparisons of POLQ family members and discuss the location of the catalytic domains. Preferred mutations disrupt the POLQ polymerase domain as depicted in FIG. 2 of Yousefzadeh and Wood, which is hereby incorporated by reference. Preferably, the POLQ mutant reduces expression and/or activity by at least 50% as compared to the wild-type gene.

Mutations in the POLQ gene can be accomplished by any of the methods well known to those in the art including random mutagenesis methods such as irradiation, random DNA integration (e.g., via a transposon or T-DNA), or by using a chemical mutagen. Moreover, in certain aspects, a POLQ gene may be mutated using a site-directed mutagenesis approach. In some embodiments, the POLQ gene is mutated or disrupted using a homologous recombination vector or a targeted nuclease such as zinc-finger nucleases (ZFNs), transcription activator-like effector nucleases (TALENs), clustered regularly interspaced short palindromic repeat (CRISPR) nucleases, or meganucleases. Preferably. the CRISPR/Cas system is used. These methods are known in the art, and one of skill will be able to identify such methods as appropriate in light of the present disclosure. Several techniques are known to screen for specific mutant alleles, e.g., Deleteagene (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc.

In a preferred embodiment, the plant cell has mutated POLQ gene, preferably both alleles are mutated. In preferred embodiments, the mutation is a "knock-out" allele, i.e., no functional protein is produced.

In some embodiments, the CRISPR/Cas system is used to reduce POLQ expression or activity. The CRISPR/Cas system is based on the RNA-guided Cas9 nuclease from the type II prokaryotic CRISPR (Clustered Regularly Interspaced Short palindromic Repeats) adaptive immune system (see, e.g., Belahj et al., Plant Methods 9:39, 2013). This system comprises three components: Cas9 protein, crRNA, and tracrRNA. The crRNA and tracrRNA are normally provided as a single RNA molecule referred to as gRNA (guideRNA). The guide RNA can be expressed using small nuclear RNA promoters such as U6 or U3. Plant codon-optimized versions of Cas9 have also been described and can be expressed in plants by either constitutive promoters (e.g. 35S promoter) or by a tissue specific or inducible promoter.

This system involves targeting Cas9 to the specific genomic locus via a gRNA. The canonical length of the gRNA is 20 bp, however, for targeting plant loci, 19-22 bp may be used. The gRNA is designed to bind to the target sequence, in this case the POLQ gene. The binding site is chosen such that the DNA targeted is followed by a PAM sequence (protospacer adjacent motif). The Cas9 protein from *Streptococcus pyogenes*, SpCas9, is often used in this system since is has a short PAM recognition sequence of NGG. Therefore, if SpCas9 is used, suitable gRNAs can be designed by screening the POLQ genomic locus for the sequence $(N)_{19-22}NGG$. An online CRISPR Design Tool is also available to identify suitable target sites (http://tools.genome-engineering.org, Ren et al).

Further information regarding the use of the CRISPR/Cas9 system for inducing mutations in plants can be found in Lowder et al. Plant Physiology 2015 169:971-985 and Belhaj et al. 2013 Plant Methods 9:39.

The reduction in POLQ expression can also be achieved using an "inhibitory nucleic acid molecule" whose presence in a cell causes the degradation of or inhibits the function, transcription, or translation of its target gene in a sequence-specific manner. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules.

In some embodiments, the nucleic acid molecule is an antisense oligonucleotide. Antisense oligonucleotides (AONs) generally inhibit their target by binding target mRNA and sterically blocking expression by obstructing the ribosome. AONs can also inhibit their target by binding target mRNA thus forming a DNA-RNA hybrid that can be a substance for RNase H. AONs may also be produced as composite structures of two or more oligonucleotides, modified oligonucleotides, oligonucleosides, oligonucleotide mimetics, or regions or portions thereof. Such compounds have also been referred to in the art as hybrids or gapmers. Methods for designing and modifying such gapmers are described in, for example, U.S. Patent Publication Nos. 20110092572 and 20100234451. AONs typically comprise between 12 to 80, preferably between 15 to 40, nucleobases. Preferably, the AONs comprise a stretch of at least 8 nucleobases having 100% complementarity with the target mRNA.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA.

Preferably, the nucleic acid molecule is a double-stranded RNAi molecule specific for mRNA encoded by the POLQ gene. Preferably, the molecule comprises a fragment of the POLQ gene to be silenced in an inverted repeat structure. The inverted repeats are separated by a spacer, often an intron. The RNAi construct is driven by a suitable promoter and transfected into a plant. Transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene. A construct including a sequence that is operably linked to a regulatory region and a transcription termination sequence and that is transcribed into an RNA that can form a double stranded RNA, can be transformed into. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945. siRNAs directed to human POLQ have been described in Ceccaldi et al. Nature. 2015 Feb. 12; 518 (7538): 258-262.

Virus-induced gene silencing (VIGS) techniques are a variation of RNAi techniques that exploits the endogenous-antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used. Tobacco rattle virus based VIGS systems are described for example, in Baulcombe, Curr. Opin. Plant Biol. 2: 109-113 (1999); Lu, et al, Methods 30: 296-303 (2003); Ratcliff, et al, The Plant Journal 25: 237-245 (2001); and U.S. Pat. No. 7,229,829.

In some embodiments, POLQ activity is reduced by providing the plant cell with a POLQ binding molecule. Preferably, POLQ activity is reduced by at least 30%, 40%, 50%, 60%, 70%, 80%, 90%, 95% or 100% as compared to a corresponding wild-type plant cell. Preferably, the POLQ binding molecule binds to POLQ and inhibits its enzyme activity and/or its ability to bind DNA.

Preferably, the POLQ binding molecule is a small molecule. Additional binding agents include antibodies as well as non-immunoglobulin binding agents, such as phage display-derived peptide binders, and antibody mimics, e.g., affibodies, tetranectins (CTLDs), adnectins (monobodies), anticalins, DARPins (ankyrins), avimers, iMabs, microbodies, peptide aptamers, Kunitz domains, aptamers and affilins. The term "antibody" includes, for example, both naturally occurring and non-naturally occurring antibodies, polyclonal and monoclonal antibodies, chimeric antibodies and wholly synthetic antibodies and fragments thereof, such as, for example, the Fab', F(ab')2, Fv or Fab fragments, or other antigen recognizing immunoglobulin fragments.

Preferably, the POLQ binding molecule is a POLQ antibody or antigen binding fragment thereof. Antibodies recognizing POLQ are commercially available (see, e.g., X3-Q588V7 [ABX] from Abmart which was generated using the TEBICHI protein).

Antibodies which bind a particular epitope can be generated by methods known in the art. For example, polyclonal antibodies can be made by the conventional method of immunizing a mammal (e.g., rabbits, mice, rats, sheep, goats). Polyclonal antibodies are then contained in the sera of the immunized animals and can be isolated using standard procedures (e.g., affinity chromatography, immunoprecipitation, size exclusion chromatography, and ion exchange chromatography). Monoclonal antibodies can be made by the conventional method of immunization of a mammal, followed by isolation of plasma B cells producing the monoclonal antibodies of interest and fusion with a myeloma cell (see, e.g., Mishell, et al., 1980). Screening for recognition of the epitope can be performed using standard immunoassay methods including ELISA techniques, radioimmunoassays, immunofluorescence, immunohistochemistry, and Western blotting (Ausubel, et al., 1992). In vitro methods of antibody selection, such as antibody phage display, may also be used to generate antibodies (see, e.g., Schirrmann et al. 2011). Preferably, a nuclear localization signal is added to the antibody in order to increase localization to the nucleus.

The present disclosure also encompasses a non-naturally occurring plant or plant cell wherein POLQ expression and/or activity in said plant or plant cell is reduced as disclosed herein, wherein said plant or plant cell is not *Arabidopsis thaliana*. In a preferred embodiment, the plant or plant cell expresses a POLQ "inhibitory nucleic acid molecule" as described herein. In a preferred embodiment, the plant or plant cell has a mutated POLQ, as described herein. Said plants and plant cells are useful for carrying out the methods disclosed herein. Accordingly, the present disclosure also encompasses the use of the plant or plant cell for transfecting a nucleic acid molecule of interest.

The present disclosure also encompasses plant cells and plants produced by the methods disclosed herein. Said plants and plant cells are advantageous since they comprise the nucleic acid molecule, but their genome has limited or no random recombination events of the nucleic acid. In preferred embodiments, said plant cells and plants have reduced expression and/or activity of POLQ as described herein.

The present disclosure also encompasses the progeny of plants produced by the methods disclosed herein. As used herein the term "progeny" denotes the offspring (including seeds) of any generation of a parent plant prepared in accordance with the methods described herein, wherein the progeny comprises the nucleic acid molecule of interest.

Definitions

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

All patent and literature references cited in the present specification are hereby incorporated by reference in their entirety.

As used herein, homologous recombination (HR) refers to error-free break repair using a non-damaged template (usually the sister chromatid).

As used herein, HDR (homology-driven repair) refers more broadly to the use of homologous sequences to direct repair using a template. A break can also be repaired if it is flanked by homologous sequences in which case the repair mode is called SSA, for single-strand annealing; this outcome is error prone.

All other repair that is not HR, HDR or SSA is usually referred to as end joining (EJ). Because EJ does not use homology to direct repair it was originally termed non-homologous end-joining (NHEJ). The best known EJ pathway, which was first discovered, required a.o. the proteins KU70 and KU80 and LIG4 and is referred to as NHEJ or classical NHEJ (cNHEJ). EJ that is not cNHEJ (that manifested in cells that were deficient for cNHEJ) is termed "alternative" EJ or alt-EJ. Because this type of EJ frequently displays segments of identical bases at the junctions of the repair product is has also been called: micro-homology-mediated EJ or MMEJ.

As used herein, TMEJ (pol Theta-Mediated EJ) refers to repair mediated by POLQ. accepted in the field. While not wishing to be bound by theory, we propose that most alt-EJ repair is actually TMEJ mediated.

The invention is further explained in the following examples. These examples do not limit the scope of the invention, but merely serve to clarify the invention.

EXAMPLES

Example 1 T-DNA Transfection

Background

*Agrobacterium tumefaciens* is the causal agent of crown gall disease in dicotyledonous plants. A piece of the pathogen's DNA, the T-DNA, is transferred to plant cells where it integrates into the genome, making it an example of trans-kingdom genetic transfer. The genes located on the T-DNA transform plant cells into tumour cells that synthesize nutrients, which the bacterium can use as a source of carbon and nitrogen, hence creating an ecological niche for itself[2]. The DNA transmission capabilities of this pathogen have been vastly explored in biotechnology as a means of inserting foreign genes into plants. Even though much is now known about the interaction between *Agrobacterium* and plant cells, and the processes leading to the integration of T-DNA into the host genome, the actual mechanism of integration has remained unknown[1]. Already two decades ago it was hypothesized that *Agrobacterium* utilises host double-strand break (DSB) repair enzymes to catalyse T-DNA integration, leading to the genetic investigation of key proteins of different DSB repair pathways[3]. Canonical non-homologous end-joining and homologous recombination factors have been investigated for their involvement in T-DNA integration, but with limited and varying results[4-7]. Even when different pathways were disabled in combination, T-DNA integration remained possible[8,9], suggesting the involvement of an unknown pathway yet to be identified.

One potentially informative feature of T-DNA integration that hints towards the integration mechanism is a type of genome scar, so-called "filler DNA", that is frequently found at sites of T-DNA integration. Filler DNAs are inserts of DNA sequences that sometimes contain stretches identical to sequences present in the immediate flank of the integration site[10,11]. We noticed a striking resemblance of filler DNA composition in T-DNA integration events to the products of error-prone DSB repair in the nematode C. elegans and the fly D. melanogaster. In these species, replication-associated as well as nuclease-induced DSBs can be repaired by an alternative end-joining pathway that critically depends on the A family polymerase Theta (Pol θ), in some cases with filler-like insertions as a consequence[12-14]. This signature feature of Pol θ-mediated End-Joining is evolutionarily conserved as also in mammalian cells DNA inserts can be found at repair sites[15,16]. Pol θ-encoding genes can be found in the genomes of all multi-cellular eukaryotes including the model plant Arabidopsis thaliana, in which the gene is called Tebichi[17,18].

To address the question whether Pol θ is responsible for filler DNA synthesis in plants and ipso facto in catalysing T-DNA integration, we transformed wild type (Col-0) plants and two knock-out alleles of Pol θ (teb-5 and teb-2[17]) by floral dip transformation. We found that transformation of wild-type Col-0 plants occurred normally, while from teb-2 and teb-5 plants not a single transformant could be recovered (FIG. 1a-c).

To exclude the possibility that these outcomes result from a non-obvious morphological flower defect that would prevent Agrobacterium from penetrating and reaching the female gametophytes (the target cells for transformation) we assayed transient expression of T-DNA in these cells. To this end, we used T-DNA expressing the marker GUS::intron under control of the ACT11 promoter, which expresses in ovules/developing seeds[19,20]. Upon infection with Agrobacterium, we found that T-DNA-mediated transient expression in wild-type and Pol θ mutant plants are indistinguishable (FIG. 1). T-DNA can thus reach the target tissue nuclei, but entirely depends on functional Pol θ for its integration.

It has previously been suggested that T-DNA integration in root cells may be different from T-DNA integration in flowers[21]. Whilst thousands of T-DNA-plant genome junctions are available for Arabidopsis flower transformants, only a limited number has been determined for transformants obtained through root transformation, making an a priori prediction impossible. Therefore, we infected Col-0 and pol θ-deficient roots with an Agrobacterium strain delivering a T-DNA that provides resistance to the herbicide phosphinothricin (PPT) and used formation of green shoots on selection plates containing PPT as a marker for stable integration. As expected, we found ~80% successful transformation in Col-0, but the frequency for transformation of pol θ-deficient roots was greatly reduced (FIG. 2a-b, f); in fact, none of 853 calli developed green shoots. Regeneration of shoots from calli under non-selective conditions was unimpaired in pol Θ-deficient roots. We noted that infected pol θ-deficient roots did form calli, but these did not grow out, and deteriorated after a few weeks, which suggest that callus formation can result from transient expression of non-integrated T-DNA. Indeed, TAIL-PCR assays directed to clone and validate T-DNA integration only yielded products in DNA extracted from infected Col-0 calli and not from infected teb-5 calli (FIG. 2c). To confirm proficiency of T-DNA delivery and transient expression in pol θ-deficient roots we showed successful expression of a T-DNA-encoded GUS::intron gene in infected teb-2 and teb-5 roots (FIG. 2d-e). From these data we conclude that for root cell transformation, as is the case for floral gametes, successful T-DNA integration depends on functional pol θ.

Figure 3:
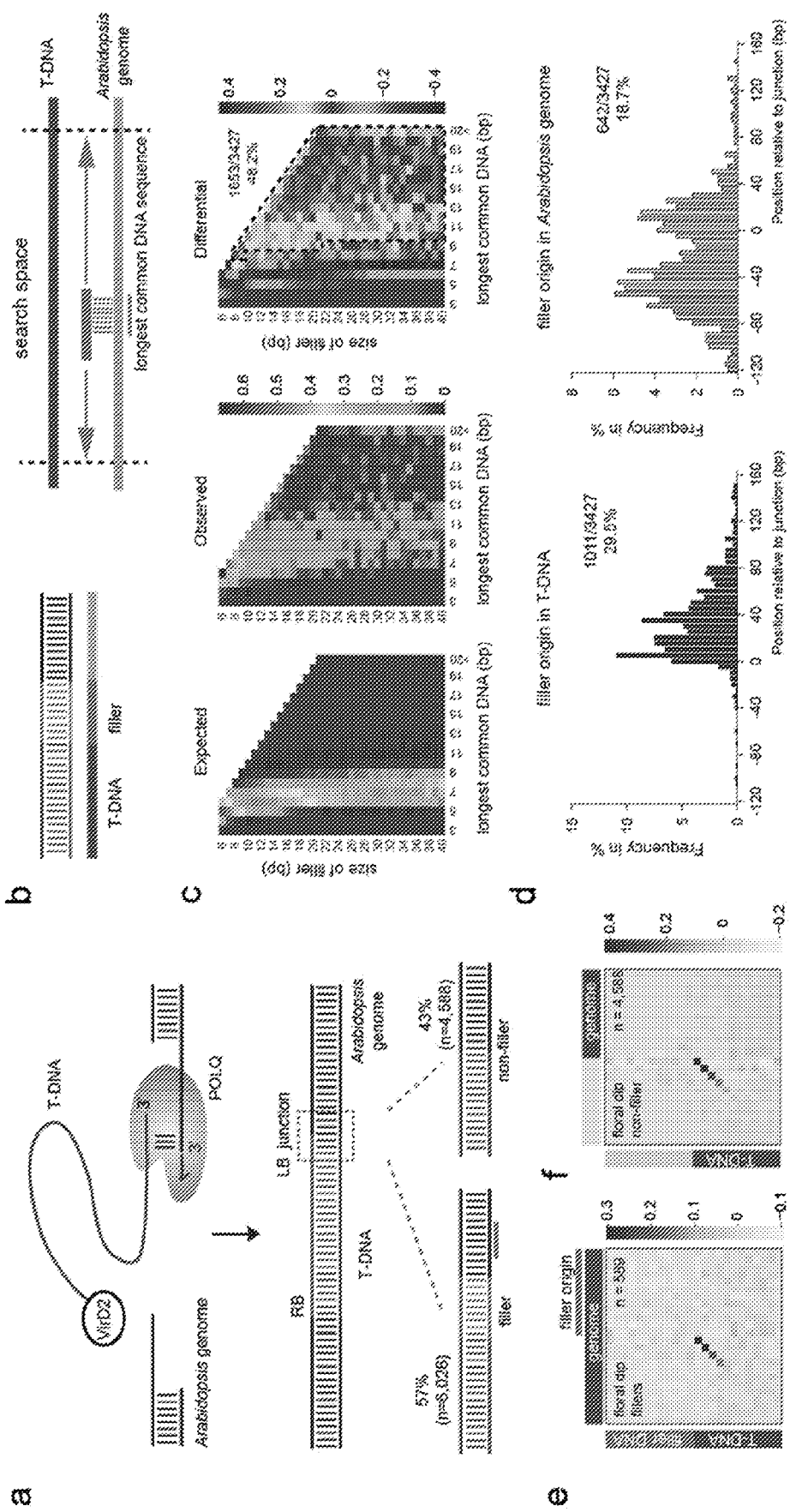
FIG. 3: Filler DNA reflects Pol θ-dependent extension of minimally paired T-DNA—*Arabidopsis* genome molecules. a, Proposed action of Pol θ in the integration of T-DNA: DNA synthesis by Pol θ stabilizes minimally paired 3' overhanging DNA ends, one end provided by the T-DNA, the other by the *Arabidopsis* genome. T-DNA-genome junctions are one of two types: ~57% of sequenced junctions contain filler DNA, whereas ~43% of sequenced alleles are without filler. b, Schematic representation of the longest common substring (LCS) analysis. For each filler (blue), the longest possible stretch of sequence identity between the filler and a target sequence is determined. c, Heat map representations of the LCSs for T-DNAs with fillers of size 6 to 40 nt. In the left panel, the pseudo-random probability (see Methods section for the approach) is plotted, while the middle panel reflects the complete data set in which the search space comprises of genomic *Arabidopsis* sequence on both sides of the T-DNA insert (~120 bp to +160 bp with respect to the junction), 160 bp of T-DNA sequence within the insert (starting from the junction) and 120 bp of the T-DNA's original flank, which is plasmid DNA. The right panel displays the data-over-probability differential, which thus visualizes over- (yellow to red) and underrepresentation (light to dark blue). From this differential heat map, the percentage of T-DNA integrations, of which their cognate fillers are >10 fold overrepresented with respect to the probability is determined to be 48.2%. d, The subcategory (n=1,653) as determined in c is used to plot the location with respect to the integration site (5 bp bin size). e, Heat map representation of filler containing T-DNA junctions in which the filler-containing junctions are plotted to their cognate filler-matching sequences in the vicinity of the junctions to visualize the degree of sequence identity. f, Heat map representation of T-DNA integration junctions that are without fillers, in which the degree of sequence identity is determined between the T-DNA and the *Arabidopsis* genome.

T-DNA is transmitted to plant cells as a single stranded DNA (ssDNA) molecule, with the bacterial VirD2 protein covalently attached to its 5' end. This end is termed the T-DNA's right border (RB). The T-DNA 3' end, the left border (LB), is unprotected, making it an excellent substrate for a pol θ-mediated repair reaction: in vitro, DNA synthesis by pol θ stabilizes two minimally paired 3' overhanging DNA ends[22]. This biochemical property of pol θ, together with its demonstrated role in repairing physiological genomic breaks, projects a remarkably simple mechanism for T-DNA integrations into the plant genome: inadvertent capture of T-DNA during repair of spontaneous genomic DSBs (FIG. 3a). The extreme sensitivity of pol θ mutant plants towards DSB-inducing agents[17] argues for a prominent role for pol θ in repairing genomic breaks. In support for endogenous DSBs acting as T-DNA capture sites, it has been found that inflicting additional DNA damage to the genome, either through ionizing radiation or by ectopic expression of endonucleases, stimulates and directs T-DNA integration[23,24].

To investigate the characteristics of pol θ action in vivo, we systematically analysed >10,000 products of its action: T-DNA/plant genome junctions resulting from integration via floral dip in wild-type plant cells[11]. In almost 70% of all integration events, one or both junctions contain filler DNA, which are largely of unknown origin. A recent survey, using stringent criteria, mapped the origin of 16% of fillers to sequences located within 10 kb of the T-DNA insertion, either in the genomic flank or in the T-DNA itself[11]. However, earlier reports have provided clues that fillers might reflect molecular patchwork in being compositions of multiple smaller segments that are of different origin[10]. We systematically analysed a collection of ~5,000 fillers using a longest common substring (LCS) strategy that determines the longest possible stretch of identity between a filler and a subject sequence (FIG. 3b). We find that ~60% of fillers have at least one match to DNA within 100 bp of the junction. In ~20% of these, we identified additional stretches mapping to other flanking positions. The templates that are used for filler synthesis are predominantly close to the junction (FIG. 3b-d), and both the T-DNA and the plant genome are used (FIG. 3d). Many fillers have complex compositions with multiple stretches that can be reliably traced, but are sometimes interspersed with nucleotides of unknown origin. These segmental sequence arrangements provide in vivo validation for the proposition that pol θ can facilitate repair by allowing one or more cycles of primer-template switching, a feature that may help to generate resolution-stimulating complementary ends. To examine whether fillers are indeed stimulated by primer-template interaction, we generated heat maps in which we plotted filler-containing junctions to their cognate filler-matching sequences in the vicinity of the junctions. This approach visualizes the degree of sequence identity between the predicted 3' end that generated a junction, i.e. the primer, and the sequence immediately upstream of the template that is used for filler synthesis. To avoid possible ambiguity in interpretation, we restricted our analysis to only those cases (n=589) for which the filler has only one contiguous match in the flank. We indeed find profound overrepresentation of matching bases (FIG. 3e): 66% of the fillers have at least a 1 nucleotide primer, 57% contain at least 2 matches between primer and template, and 47% have 3 priming nucleotides at the 3' terminus. Together these results suggests i) that filler DNA is the product of pol θ extending the 3' end of a genomic break that is minimally base-paired with a 3' end of the T-DNA, or vice versa, and ii) that the primer-template switching ability of this polymerase is responsible for the complex composition of fillers.

Interestingly, a heat map that portrays the degree of microhomology for T-DNA junctions without fillers (which also require pol θ for their formation) is very similar to the primer-template heat map of filler-containing junctions (FIG. 3e, f). This notion supports the idea that microhomology in DSB repair does not reflect a marginally increased stability in pairing non-complementary ssDNA strands, but instead reflects the biochemical property of a polymerase to preferentially extend a 3' end paired to a small number of complementary bases.

Figure 4A:
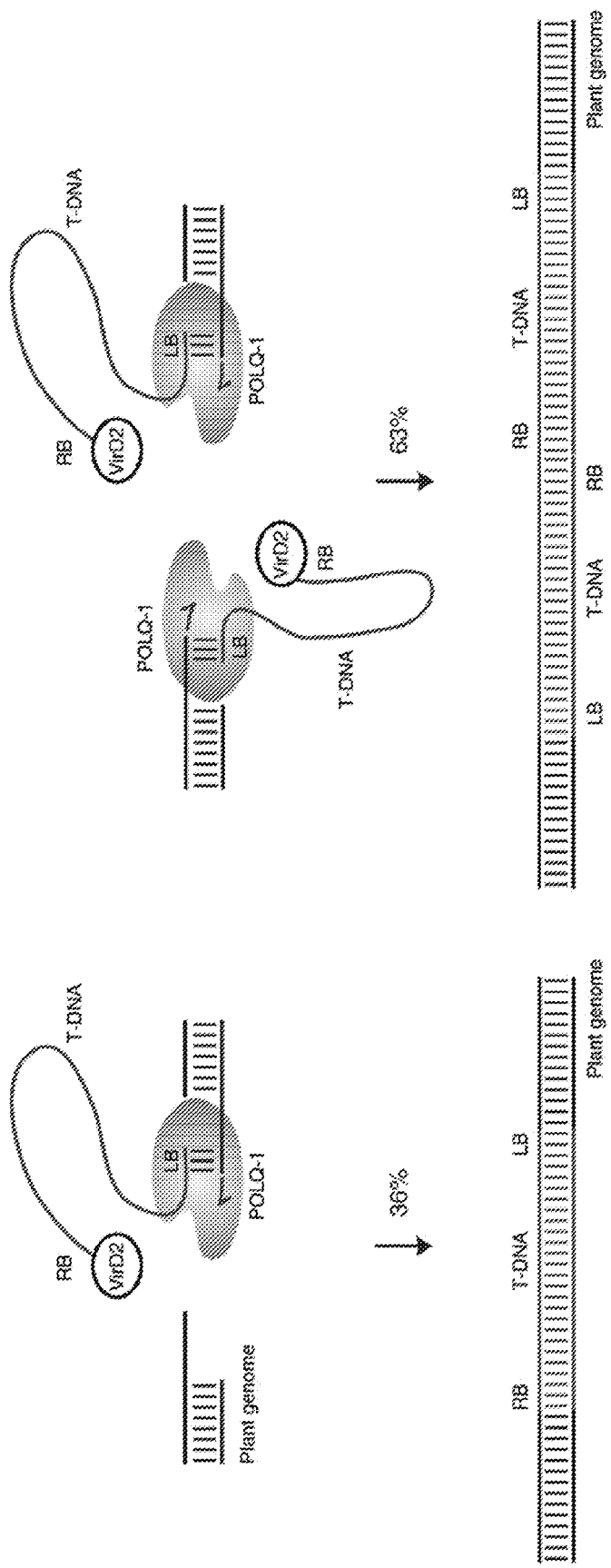
FIG. 4. A model for T-DNA integration. a, the T-DNA is preferentially captured at the 3' end, where pol Θ can extend from priming by minimal base pairing. Subsequent 5' end capture by the genome results in a single T-DNA insert in the genome (left picture). However, in most cases (63%), double integrations are observed where both T-DNAs are in an inverted orientation, which points towards the preferential capture of a T-DNAs 3'end by the plant genome. b, after capture of the 3' end of a T-DNA, iterative cycles of priming, extending, and primer-template switching will result in T-DNA insertions with patched work fillers carrying multiple templated insertions.
Figure 4B:
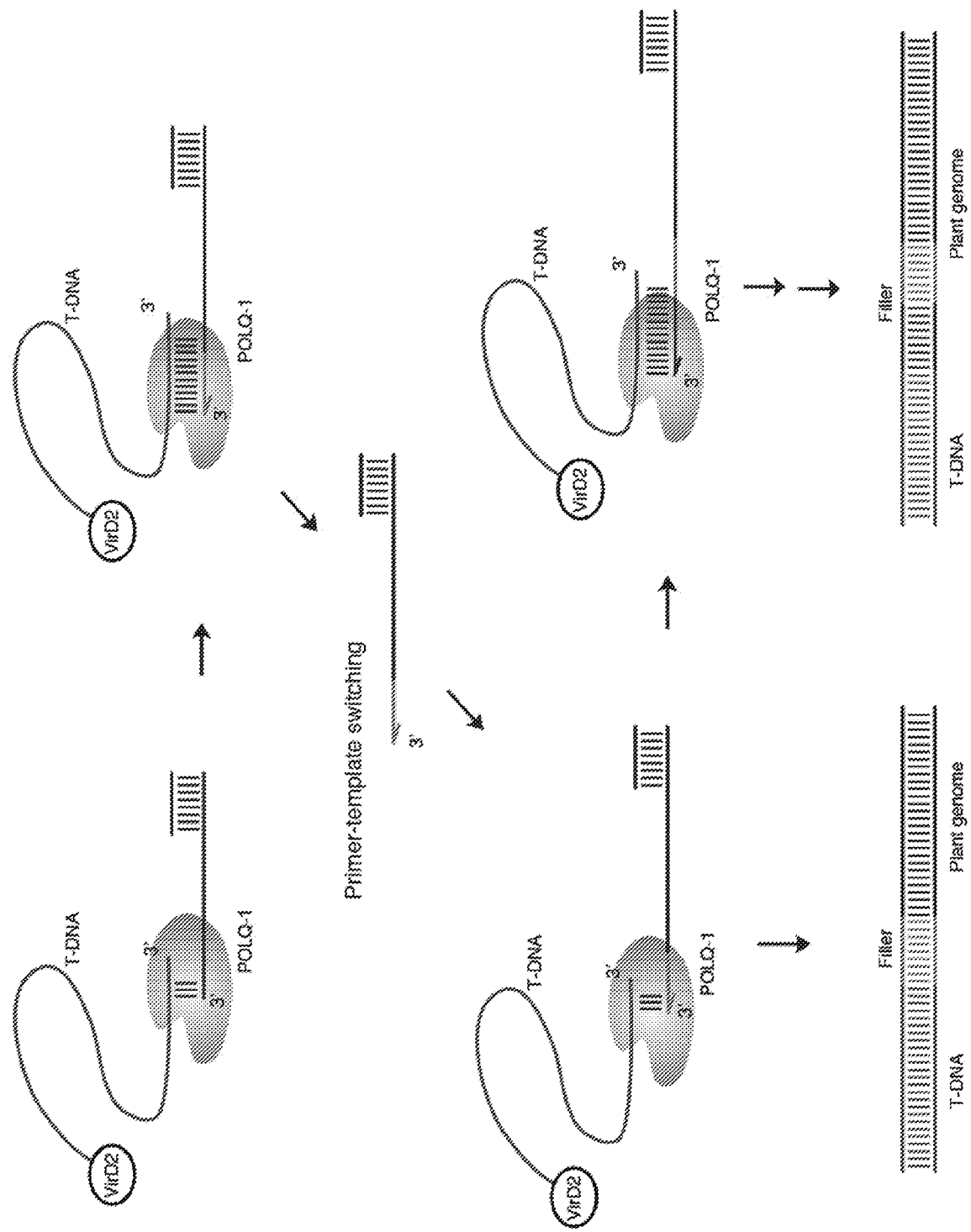

Collectively our results lead to a conceptually simple mechanism for T-DNA integration into plant genomes: the plant's pol θ-mediated repair pathway, instead of joining the ends of a genomic break, joins the ends to exogenously provided T-DNA molecules. The outcome is similar in germ cells and in somatic cells. Most T-DNA integrations (63%) have an inverted repeat configuration, where on either side the plant genome is attached to the 3' LB of a T-DNA, arguing that the 3' end of the T-DNA is the preferential substrate. The ability of pol θ to extend minimally paired 3' ends provides a mechanistic explanation for the attachment of the T-DNA left border to the plant genome, whilst its tolerance to primer-template switching can explain the existence of patchwork fillers (see FIG. 4). The question how the 5' right border of the T-DNA is connected either to the plant genome (for a single copy integration) or to another T-DNA 5' border (for the inverted repeat orientation) is less clear. Detailed analysis of RB-T-DNA/plant genome junctions, however, suggests a very similar mechanism of attachment: also here fillers, indicative of pol θ action, are found. It may be that a conversion of the single-stranded T-DNA to a double-stranded configuration precedes this reaction, either initiated by the genomic capture of the T-DNA's 3' end or through a yet unknown mechanism[25,26]. An intriguing notion is that a DSB that captures the 3' end of a T-DNA at either side is protected from 5' resection activity by the covalently attached bacterial VirD2 protein. For resolution, this 5' end may require additional enzymatic processing, which may explain the reduced integration efficiencies in plants carrying mutations in various DNA processing enzymes[4-9].

Apart from providing a mechanistic understanding of T-DNA integration in plants, our data has profound impact on biotechnological strategies to develop transgenic crops: targeting pol θ will completely abolish unwanted random integration in gene-targeting approaches whilst not affecting HR-pol θ is not required for HR in all species thus far examined. The absolute dependence on pol θ for T-DNA integration in *Arabidopsis* gametophytes as well as in roots, together with the ample appearance of pol θ signatures upon T-DNA integration in all higher plants studied, including crop species such as rice, tomato, strawberry or tobacco, projects broad utility[27-30].

Methods

Plant Lines and Growth Conditions Insertion mutant information was obtained from the SIGnAL website at http://signal.salk.edu. teb-5 (SALK_018851) and teb-2 (SALK_035610) were obtained from the SALK T-DNA collection[31]. The teb-5 and teb-2 alleles have been described previously[17]. Plants were grown on soil at 20° C. in a 16 hours light/8 hours dark cycle.

Floral Dip Transformation

Wild type (ecotype Col-0) and mutant *Arabidopsis* plants were transformed using disarmed *Agrobacterium* strain LBA1100[32] harbouring binary vector pCAMBIA1301 by the floral dip method as previously described[33]. Transgenic seeds were selected on MA solid medium lacking sucrose, supplemented with 100 μg/mL nystatin, 100 μg/mL timentin (to kill off any remaining *Agrobacterium* and prevent infections) and 15 μg/mL hygromycin to select for integration events. Alternatively, plants were transformed using *A. tumefaciens* strain AgII[34] harbouring binary vector pSDM3900[36]. Transgenic seeds were selected on MA solid medium without sucrose supplemented with 100 μg/mL nystatin, 100 μg/mL timentin (to kill off any remaining *Agrobacterium* and prevent infections) and 15 μg/mL phosphinothricin to select for integration events. To detect transient events, flowering plants were subjected to floral dip by *Agrobacterium* strain Agll harbouring pCAMBIA1301_ACT11, which was made by cloning an 850 bp fragment from the Col-0 genome containing the ACT11 promoter into binary vector pCAMBIA1301, from which the stable integration marker and its promoter has been removed (sequence available upon request). After 6 days, flowers were collected and stained overnight in phosphate buffer (pH=7.3) containing 1 mM $K_3Fe(CN)_6$ and 1 mM $K_4Fe(CN)_6$, 10 mM $Na_2EDTA$, 0.1% SDS, 0.1% Triton X-100 and 2 mM X-gluc. Afterwards, the flowers were cleared using 70% ethanol.

Root Transformation

Root transformations were performed on wild type (Col-0) and mutant *A. thaliana* plants as described previously[36], using disarmed *A. tumefaciens* strain LBA1100[32] harbouring binary vector pCAMBIA3301. After two days of cocultivation, part of the root explants were stained immediately in phosphate buffer (pH=7.3) containing 1 mM $K_3Fe(CN)_6$ and 1 mM $K_4Fe(CN)_6$, 10 mM $Na_2EDTA$, 0.1% SDS, 0.1% Triton X-100 and 2 mM X-gluc, while the rest of the root explants were transferred to solid medium containing 10 μg/mL PPT for selection for transformants and 500 μg/mL carbenicillin and 100 μg/mL vancomycin to kill off remaining *Agrobacterium*.

Amplification of Insertion Junctions

Plant material was disrupted to a powder in a TissueLyser (Retch, Haan Germany) under liquid $N_2$. DNA was isolated as previously described[37]. 1 μL isolated DNA was used for PCR in a total volume of 20 μL. Taq polymerase and buffers were made in-house. T-DNA-genome junctions were isolated by TAIL-PCR[38], using degenerate primer AD2 (NGTCGASWGANAWGAA(SEQ. ID NO:1))[38], and specific nested primers:

| | | |
|---|---|---|
| LB0 | GTCTGGACCGATGGCTGTGTAGAAGTA (SEQ ID NO: 2)[38] | floral dip, LB |
| LB1 | GAAGTACTCGCCGATAGTGGAAACC (SEQ ID NO: 3)[38] | floral dip, LB |
| LB2 | GTGAGTAGTTCCCAGATAAGGGAATTAG (SEQ ID NO: 4)[38] | floral dip, LB |
| LB0 pC3301 | CAAGCACGGGAACTGGCATGACGTG (SEQ ID NO: 5) | root transformation, LB |
| LB1 pC3301 | GTCCTGCCCGTCACCGAGATTTGAC (SEQ ID NO: 6) | root transformation, LB |

-continued

| | | |
|---|---|---|
| LB2 | GTGAGTAGTTCCCAGATAAGGGAATTAG (SEQ ID NO: 7)[38] | root transformation, LB |
| RB0 | GGCAATAAAGTTTCTTAAGATTGAATCCTGT (SEQ ID NO: 8)[9] | root transformation, RB |
| RB1 | TGTTGCCGGTCTTGCGATGATTATCA (SEQ ID NO: 9)[9] | root transformation, RB |
| RB2 | GTAATGCATGACGTTATTTATGAGATGGGTT (SEQ ID NO: 10)[9] | root transformation, RB |

Determination of Genomic Insertions of T-DNA

All T-DNA integration confirmation sequences were downloaded from ENA/GenBank (accession numbers LN484267 through LN515397)[11]. To determine T-DNA insertion junctions, MegaBLAST searches were performed between each sequence and the *Arabidopsis* reference genome (TAIR10) and the relevant binary plasmid. For sequences where the T-DNA was present at the 3' region, the reverse complement of the sequence was further analysed. To focus on high quality sequenced junctions, we only included sequences where the 3' end of the T-DNA, as well as the 5' genomic region, showed a perfect match (≥20 bp, no mismatch, no gap) to its corresponding best BLAST hit. Sequences where T-DNA and genomic BLAST hits were non-overlapping were designated as filler integration, while sequences that had an overlapping or joining BLAST hit were designated as non-filler integration. Fillers containing non-informative bases were removed. After applying these filters 10,616 T-DNA insertion events remained for further analysis.

Origin of Fillers

To determine the origin of fillers we employed a longest common substring (LCS) algorithm. The algorithm determines the longest common sequence between the filler (query) and another sequence (subject). For each filler (≥6 bp and ≤40 bp) we determined the LCS in both the T-DNA and the *Arabidopsis* reference genome, in both strand orientations, relative to the T-DNA genome junction position that was determined by its respective best BLAST hits. We searched the T-DNA plasmid sequence and the reference genome 25-6,400 bases away from the junction in both directions. To calculate the overrepresentation of found LCS lengths we determined the pseudo-random probability of finding an LCS of a certain length for a given filler in a DNA sequence. To this end we shuffled the DNA of the subject for each filler and searched for the LCS (10-100 times for each filler). A probability distribution of pseudo-random LCS lengths was then created for each filler size (≥6 bp and ≤40 bp). Overrepresentation between the probability distribution and the actual found LCS size is calculated as the fraction of fillers that have an LCS length at the right tail of the probability distribution minus the fraction of expected fillers. We marked individual fillers as overrepresented when the actual distribution of its LCS length was at least ten times greater than the probability.

To determine whether a filler originated from the T-DNA originating plasmid we made use of the LCS with the addition that the location was only used if the LCS was of length ≥13 bp. To identify possible filler origins in the *Arabidopsis* genome we used BLAST with a cut-off E-value of $10^{-4}$.

Example 2: Homologous Recombination

Example 1 demonstrates that functional Pol θ is required for stable, random integration of T-DNA. The present example demonstrates that functional Pol θ is not required for stable integration via homologous recombination.

A T-DNA construct is prepared, containing around 6 kb of homology to the endogenous *Arabidopsis* locus protophorphyrinogen oxidase (PPO). The homologous region contains two point mutations, which confer resistance to the herbicide butafenicil upon integration via homologous recombination at the PPO locus (see Hanin et al, Plant J 2001 for a description of the mutations). In addition, the T-DNA encodes a Cas9 enzyme (*Arabidopsis* codon-optimized Cas9-AteCas9 (Fauser et al. Plant J 79:348-359 2014)) and guide RNA, directing the Cas9 enzyme to the PPO locus. The expression of Cas9 is driven by the ubiquitin promoter and the guide RNA is under control of the U6 (AtU6) promoter.

Wild type (Col-0) plants and two knock-out alleles of Pol θ (teb-5 and teb-2[17]) are transformed by floral dip transformation. Stable integration of the T-DNA via homologous recombination is measured by resistance against butafenicil.

The level of stable integration at the site specific locus between wild-type and Pol θ mutant plants will be similar.

Example 3: Transfection with a Linearized Plasmid

A plasmid is prepared, containing around 6 Kb of homology to the endogenous *Arabidopsis* locus protophorphyrinogen oxidase (PPO). The homologous region contains two point mutations, which confer resistance to the herbicide butafenicil upon integration via homologous recombination at the PPO locus (see Hanin et al, Plant J 2001 for a description of the mutations). In addition, the plasmid encodes a Cas9 enzyme (*Arabidopsis* codon-optimized Cas9-AteCas9 (Fauser et al. Plant J 79:348-359 2014)) and guide RNA, directing the Cas9 enzyme to the PPO locus. The expression of Cas9 is under control of the ubiquitin promoter and the guide RNA is under control of the U6 (AtU6) promoter. The plasmid also contains a unique restriction site. The plasmid is linearized by digestion with the appropriate restriction site.

Protoplasts are prepared from WT and Pol θ-deficient plants (teb-5 and teb-2) and the linearized plasmid is transformed into the protoplasts by a standard PEG transformation protocol. Colonies are maintained in butafenicil-containing medium to selected for stable integration events via homologous recombination. The level of stable integration at the site specific locus between wild-type and Pol θ mutant plants will be similar.

Example 4: Transfection of Tomato Plant

The present example will demonstrate the reduction of random integration in a crop plant, namely tomato (*Solanum lycopersum*). The POLQ gene from tomato was identified from the NCBI database as accession no. XP_010325163 based on a BLAST search using the Tebichi sequence.

Pol Θ-deficient tomato mutants are created by targeting the Pol Θ locus using CRISPR and self-pollinating to create homozygous mutants in the next generation. Briefly, a T-DNA construct is prepared encoding a kanamycin-selectable marker, a Cas9 enzyme (plant codon-optimized Cas9-pcoCas9 (Li et al. 2013 Nat Biotechnol 31:688-691)) and guide RNA, directing the Cas9 enzyme to the POLQ locus. The expression of Cas9 is under control of the 35S promoter and the guide RNA is under control of the U3 (AtU3) promoter. Tomato cotyledon explants are transformed by immersion in *Agrobacterium* suspension, selected for kanamycin resistance, and screened for POLQ mutations.

Plantlets are screened for POLQ mutations using the Surveyor assay (Voytas 2013 Annu Rev Plant Biol 64:327-350) and plantlets containing an inactivating mutation in POLQ are grown and self-pollinated to create homozygous mutants in the next generation.

The effect of POLQ on random integration is demonstrated using a tumor assay performed on wild-type tomato plants and on Pol Θ-deficient tomato mutants. Briefly, *Agrobacterium* is inserted into a hole in the stem of wild-type tomato plants and pol Θ-deficient tomato plants. Random integration is measured by measuring tumor formation. WT tomato plants will develop tumors—indicating random integration events, while pol Θ-deficient tomato plants will not develop tumors.

Example 5: Generation of polQ Deficient Crop Plants

A crop plant, e.g. wheat, soybean, rice, cotton, corn or brassica plant having a mutation in one or more polQ genes (e.g. in one or more homologous genes) is identified or generated via (random) mutagenesis or targeted knockout (e.g. using a sequence specific nuclease such as a meganuclease, a zinc finger nuclease, a TALEN, Crispr/Cas9, Crispr/Cpf1 etc). Reduction in PolQ expression and/or activity is confirmed by Q-PCR, western blotting or the like.

A crop plant, e.g. wheat, soybean, rice, cotton or brassica plant, is transformed with a construct encoding a polQ inhibitory nucleic acid molecule or polQ binding molecule (e.g. encoding a polQ hairpin RNA, antibody, etc, under control of a constitutive or inducible promoter). Reduction in PolQ expression and/or activity is confirmed by Q-PCR, western blotting or the like.

Example 6: Transfection of polQ Deficient Crop Plants with a Selectable Marker Gene A plant of Example 5 having reduced PolQ expression, as well as a corresponding plant having wildtype polQ expression are transformed with a selectable marker gene (e.g. bar, gus) using *Agrobacterium*, according to methods well known in the art.

Transformants are screened for expression of the selectable marker gene.

Transformants with reduced polQ expression show transient expression of the selectable marker gene, while transformants with wildtype polQ expression show stable expression of the selectable marker gene.

Genomic integration of the selectable marker gene is evaluated via e.g. southern blotting of genomic DNA isolated from transformed plants with wildtype or reduced polQ expression. The presence of the selectable marker gene can be detected in the genomic DNA of polQ-wildtype plants, while plants with reduced polQ expression show less or even no genomic integration of the selectable marker gene.

Example 7: Targeted Insertion Via Homologous Recombination in polQ Deficient Crop Plants PolQ deficient plants of Example 5 and corresponding plants having wildtype polQ expression are transformed with a nucleic acid of interest for targeted integration via homologous recombination. The nucleic acid of interest comprises sequences homologous to the genomic DNA at the genomic target site. Optionally, the plant is cotransformed with an expression construct for a sequence specific nuclease capable of inducing a DNA break at the target site to enhance homologous recombination. Plants are screened for integration of the nucleic acid of interest by e.g. southern blotting or PCR. Plants having wild-type polQ expression show random insertion of nucleic acid of interest as well as targeted insertion via homologous recombination at the target site. Plants with reduced polQ expression show less or even no random insertion of the nucleic acid of interest, but do show targeted insertion via homologous recombination of the nucleic acid of interest at the target site.

REFERENCES

1. Gelvin, S. B. Plant proteins involved in *Agrobacterium*-mediated genetic transformation. *Annu Rev Phytopathol* 48, 45-68
2. Zhu, J. et al. The bases of crown gall tumorigenesis. *J Bacteriol* 182, 3885-3895 (2000).
3. Tinland, B. The integration of T-DNA into plant genomes. *Trends Plant Sci.* 1, 178-184 (1996).
4. Gallego, M. E., Bleuyard, J.-Y., Daoudal-Cotterell, S., Jallut, N. & White, C. I. Ku80 plays a role in non-homologous recombination but is not required for T-DNA integration in *Arabidopsis*. *Plant J.* 35, 557-65 (2003).
5. Friesner, J. & Britt, A. B. Ku80- and DNA ligase IV-deficient plants are sensitive to ionizing radiation and defective in T-DNA integration. *Plant J.* 34, 427-40 (2003).
6. Van Attikum, H. et al. The *Arabidopsis* AtLIG4 gene is required for the repair of DNA damage, but not for the integration of *Agrobacterium* T-DNA. *Nucleic Acids Res.* 31, 4247-55 (2003).
7. Li, J. et al. Involvement of KU80 in T-DNA integration in plant cells. *Proc Natl Acad Sci USA* 102, 19231-19236 (2005).
8. Mestiri, I., Norre, F., Gallego, M. E. & White, C. I. Multiple host-cell recombination pathways act in *Agrobacterium* mediated transformation of plant cells. *Plant J.* (2013). doi: 10.1111/tpj. 12398
9. Park, S.-Y. et al. *Agrobacterium* T-DNA integration into the plant genome can occur without the activity of key non-homologous end-joining proteins. *Plant J.* (2015). doi: 10.1111/tpj. 12779
10. Windels, P., De Buck, S., Van Bockstaele, E., De Loose, M. & Depicker, A. T-DNA integration in *Arabidopsis* chromosomes. Presence and origin of filler DNA sequences. *Plant Physiol* 133, 2061-2068 (2003).
11. Kleinboelting, N. et al. The structural features of thousands of T-DNA insertion sites are consistent with a double-strand break repair based insertion mechanism. *Mol. Plant* (2015). doi: 10.1016/j.molp.2015.08.011
12. Chan, S. H., Yu, A. M. & McVey, M. Dual roles for DNA polymerase theta in alternative end-joining repair of double-strand breaks in *Drosophila*. *PLoS Genet.* 6, e1001005 (2010).
13. Roerink, S. F., van Schendel, R. & Tijsterman, M. Polymerase theta-mediated end joining of replication-associated DNA breaks in *C. elegans*. *Genome Res.* (2014). doi:10.1101/gr.170431.113
14. Koole, W. et al. A Polymerase Theta-dependent repair pathway suppresses extensive genomic instability at endogenous G4 DNA sites. *Nat. Commun.* 5, 3216 (2014).
15. Mateos-Gomez, P. A. et al. Mammalian polymerase θ promotes alternative NHEJ and suppresses recombination. *Nature* (2015). doi: 10.1038/nature 14157
16. Yousefzadeh, M. J. et al. Mechanism of Suppression of Chromosomal Instability by DNA Polymerase POLQ. *PLoS Genet.* 10, e1004654 (2014).

17. Inagaki, S. et al. *Arabidopsis* TEBICHI, with helicase and DNA polymerase domains, is required for regulated cell division and differentiation in meristems. *Plant Cell* 18, 879-92 (2006).
18. Yousefzadeh, M. J. & Wood, R. D. DNA polymerase POLQ and cellular defense against DNA damage. *DNA Repair (Amst)*. 12, 1-9 (2013).
19. Desfeux, C., Clough, S. J. & Bent, A. F. Female reproductive tissues are the primary target of *Agrobacterium*-mediated transformation by the *Arabidopsis* floral-dip method. *Plant Physiol* 123, 895-904 (2000).
20. Huang, S., An, Y. Q., McDowell, J. M., McKinney, E. C. & Meagher, R. B. The *Arabidopsis* ACT11 actin gene is strongly expressed in tissues of the emerging inflorescence, pollen, and developing ovules. *Plant Mol. Biol.* 33, 125-39 (1997).
21. De Buck, S., Podevin, N., Nolf, J., Jacobs, A. & Depicker, A. The T-DNA integration pattern in *Arabidopsis* transformants is highly determined by the transformed target cell. *Plant J.* 60, 134-45 (2009).
22. Kent, T., Chandramouly, G., McDevitt, S. M., Ozdemir, A. Y. & Pomerantz, R. T. Mechanism of microhomology-mediated end-joining promoted by human DNA polymerase θ. *Nat. Struct. Mol. Biol.* (2015). doi: 10.1038/nsmb.2961
23. Kohler, F., Cardon, G., Pohlman, M., Gill, R. & Schieder, O. Enhancement of transformation rates in higher plants by low-dose irradiation: Are DNA repair systems involved in the incorporation of exogenous DNA into the plant genome? *Plant Mol. Biol.* 12, 189-99 (1989).
24. Salomon, S. & Puchta, H. Capture of genomic and T-DNA sequences during double-strand break repair in somatic plant cells. *EMBO J.* 17, 6086-95 (1998).
25. Tzfira, T., Frankman, L. R., Vaidya, M. & Citovsky, V. Site-specific integration of *Agrobacterium tumefaciens* T-DNA via double-stranded intermediates. *Plant Physiol* 133, 1011-1023 (2003).
26. Chilton, M. D. & Que, Q. Targeted integration of T-DNA into the tobacco genome at double-stranded breaks: new insights on the mechanism of T-DNA integration. *Plant Physiol* 133, 956-965 (2003).
27. Zhu, Q.-H., Ramm, K., Eamens, A. L., Dennis, E. S. & Upadhyaya, N. M. Transgene structures suggest that multiple mechanisms are involved in T-DNA integration in plants. *Plant Sci.* 171, 308-22 (2006).
28. Thomas, C. M. & Jones, J. D. Molecular analysis of *Agrobacterium* T-DNA integration in tomato reveals a role for left border sequence homology in most integration events. *Mol Genet Genomics* 278, 411-420 (2007).
29. Oosumi, T., Ruiz-Rojas, J. J., Veilleux, R. E., Dickerman, A. & Shulaev, V. Implementing reverse genetics in Rosaceae: analysis of T-DNA flanking sequences of insertional mutant lines in the diploid strawberry, Fragaria vesca. *Physiol. Plant.* 140, 1-9 (2010).
30. Singer, K., Shiboleth, Y. M., Li, J. & Tzfira, T. Formation of complex extrachromosomal T-DNA structures in *Agrobacterium tumefaciens*-infected plants. *Plant Physiol.* 160, 511-22 (2012).
31. Alonso, J. M. et al. Genome-wide insertional mutagenesis of *Arabidopsis thaliana. Science* 301, 653-7 (2003).
32. Beijersbergen, A., Dulk-Ras, A. D., Schilperoort, R. A. & Hooykaas, P. J. Conjugative Transfer by the Virulence System of *Agrobacterium tumefaciens. Science* (80-). 256, 1324-1327 (1992).
33. Clough, S. J. & Bent, A. F. Floral dip: a simplified method for *Agrobacterium*-mediated transformation of *Arabidopsis thaliana. Plant J* 16, 735-743 (1998).
34. Lazo, G. R., Stein, P. A. & Ludwig, R. A. A DNA transformation-competent *Arabidopsis* genomic library in *Agrobacterium. Biotechnol.* (N Y) 9, 963-967 (1991).
35. De Pater, S., Pinas, J. E., Hooykaas, P. J. J. & van der Zaal, B. J. ZFN-mediated gene targeting of the *Arabidopsis* protoporphyrinogen oxidase gene through *Agrobacterium*-mediated floral dip transformation. *Plant Biotechnol. J.* 11, 510-5 (2013).
36. Vergunst, A. C. et al. VirB/D4-dependent protein translocation from *Agrobacterium* into plant cells. *Science* (80-). 290, 979-982 (2000).
37. De Pater, S., Neuteboom, L. W., Pinas, J. E., Hooykaas, P. J. & van der Zaal, B. J. ZFN-induced mutagenesis and gene-targeting in *Arabidopsis* through *Agrobacterium*-mediated floral dip transformation. *Plant Biotechnol J* 7, 821-835 (2009).
38. Liu, Y. G., Mitsukawa, N., Oosumi, T. & Whittier, R. F. Efficient isolation and mapping of *Arabidopsis thaliana* T-DNA insert junctions by thermal asymmetric interlaced PCR. *Plant J* 8, 457-463 (1995).

The invention claimed is:

1. A method for reducing integration of transfected nucleic acid molecules in a plant cell, said method comprising:
   (a) providing a plant cell, wherein POLQ expression and/or activity in said plant cell is reduced as compared to a wild-type plant cell due to a mutation of the PolQ gene or a direct targeting of PolQ expression and/or activity; and
   (b) transfecting said plant cell with a nucleic acid molecule, wherein the transfected nucleic acid molecule comprises T-DNA, and wherein the transfection produces a plant cell wherein integration of the transfected nucleic acid molecule is reduced.

2. A method for producing a plant, comprising:
   (a) providing a plant cell, wherein POLQ expression and/or activity in said plant cell is reduced as compared to a wild-type plant cell due to a mutation of the PolQ gene or a direct targeting of PolQ expression and/or activity;
   (b) transfecting said plant cell with a nucleic acid molecule, wherein the transfected nucleic acid molecule comprises T-DNA and wherein the transfection produces a plant cell wherein integration of the transfected nucleic acid molecule is reduced; and
   (c) generating the plant from said plant cell.

3. The method according to claim 1, wherein said nucleic acid molecule is transiently transfected into the plant cell.

4. The method according to claim 1, wherein said plant cell comprises an antisense oligonucleotide specific for a pre-mRNA encoded by the POLQ gene or a double-stranded RNAi molecule specific for mRNA encoded by the POLQ gene.

5. The method according to claim 1, wherein the plant cell has one or more mutated POLQ alleles such that POLQ expression and/or activity is reduced by at least 70% as compared to the wild-type gene.

6. The method according to claim 1, wherein said plant cell is not *Arabidopsis thaliana*.

7. A plant produced by the method of claim 2, wherein the plant comprises said transfected nucleic acid molecule, and wherein said plant or plant cell is not *Arabidopsis thaliana*.

8. The progeny of a plant according to claim 7, wherein said progeny comprises said nucleic acid molecule.

9. The method of claim 1, wherein POLQ activity and/or expression is reduced in the plant cell of step a) by mutating one or more POLQ alleles in the plant cell or providing the plant cell with a POLQ inhibitory nucleic acid molecule or POLQ binding molecule.

10. The method according to claim 2, wherein said plant cell is not *Arabidopsis thaliana*.

11. The method according to claim 4, wherein said plant cell is not *Arabidopsis thaliana*.

12. The method according to claim 1, wherein POLQ expression in said plant cell of step a) is reduced by mutating one or more POLQ alleles using irradiation, a chemical mutagen, random integration using a transposon, site-directed mutagenesis, a homologous recombination vector, or a targeted nuclease.

13. The method according to claim 1, wherein POLQ expression in said plant cell of step a) is reduced by providing the plant cell with a POLQ inhibitory nucleic acid molecule, wherein the POLQ inhibitory nucleic acid molecule directly targets POLQ.

14. The method according to claim 1, wherein POLQ activity in said plant cell of step a) is reduced by providing the plant cell with a POLQ binding molecule, wherein the POLQ binding molecule binds to POLQ and inhibits its enzyme activity and/or its ability to bind DNA.

\* \* \* \* \*

SEQUENCE LISTING

```
<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: degenerated primer
<220> FEATURE:
<221> NAME/KEY: misc_feature
<222> LOCATION: (10)..(10)
<223> OTHER INFORMATION: n is a, c, g, or t

<400> SEQUENCE: 1
gtcgaswgan awgaa                                                      15

<210> SEQ ID NO 2
<211> LENGTH: 27
<212> TYPE: DNA
<213> ORGANISM: Artificial Sequence
<220> FEATURE:
```

<223> OTHER INFORMATION: nested primer

<400> SEQUENCE: 2
gtctggaccg atggctgtgt agaagta                                27

<210> SEQ ID NO 3
<211> LENGTH: 25
<212> TYPE: DNA
<213> ORGANISM: Artificial Sequence
<220> FEATURE:
<223> OTHER INFORMATION: nested primer

<400> SEQUENCE: 3
gaagtactcg ccgatagtgg aaacc                                  25

<210> SEQ ID NO 4
<211> LENGTH: 28
<212> TYPE: DNA
<213> ORGANISM: Artificial Sequence
<220> FEATURE:
<223> OTHER INFORMATION: nested primer

<400> SEQUENCE: 4
gtgagtagtt cccagataag ggaattag                               28

<210> SEQ ID NO 5
<211> LENGTH: 25
<212> TYPE: DNA
<213> ORGANISM: Artificial Sequence
<220> FEATURE:
<223> OTHER INFORMATION: nested primer

<400> SEQUENCE: 5
caagcacggg aactggcatg acgtg                                  25

<210> SEQ ID NO 6
<211> LENGTH: 25
<212> TYPE: DNA
<213> ORGANISM: Artificial Sequence
<220> FEATURE:
<223> OTHER INFORMATION: nested primer

<400> SEQUENCE: 6
gtcctgcccg tcaccgagat ttgac                                  25

<210> SEQ ID NO 7
<211> LENGTH: 28
<212> TYPE: DNA
<213> ORGANISM: Artificial Sequence
<220> FEATURE:
<223> OTHER INFORMATION: nested primer

<400> SEQUENCE: 7
gtgagtagtt cccagataag ggaattag                               28

<210> SEQ ID NO 8
<211> LENGTH: 31
<212> TYPE: DNA
<213> ORGANISM: Artificial Sequence
<220> FEATURE:
<223> OTHER INFORMATION: nested primer

<400> SEQUENCE: 8
ggcaataaag tttcttaaga ttgaatcctg t                           31

```
<210> SEQ ID NO 9
<211> LENGTH: 26
<212> TYPE: DNA
<213> ORGANISM: Artificial Sequence
<220> FEATURE:
<223> OTHER INFORMATION: nested primer

<400> SEQUENCE: 9
tgttgccggt cttgcgatga ttatca                                          26

<210> SEQ ID NO 10
<211> LENGTH: 31
<212> TYPE: DNA
<213> ORGANISM: Artificial Sequence
<220> FEATURE:
<223> OTHER INFORMATION: nested primer

<400> SEQUENCE: 10
gtaatgcatg acgttattta tgagatgggt t                                    31
```